(12) United States Patent
Horowitz et al.

(10) Patent No.: US 12,193,692 B2
(45) Date of Patent: Jan. 14, 2025

(54) ASPIRATION CATHETERS AND METHODS OF USE THEREOF

(71) Applicant: Retriever Medical, Inc., Irvine, CA (US)

(72) Inventors: Michael Bruce Horowitz, Naples, FL (US); Benjamin William Bobo, Las Vegas, NV (US); Brandon Matthew Repko, Mars, PA (US); Jack Berkman Sattell, Cambridge, MA (US)

(73) Assignee: Retriever Medical, Inc., Las Vegas, NV (US)

( * ) Notice: Subject to any disclaimer, the term of this patent is extended or adjusted under 35 U.S.C. 154(b) by 394 days.

(21) Appl. No.: 17/809,531

(22) Filed: Jun. 28, 2022

(65) Prior Publication Data

US 2022/0395286 A1    Dec. 15, 2022

Related U.S. Application Data

(63) Continuation-in-part of application No. 17/572,138, filed on Jan. 10, 2022, now Pat. No. 11,382,643, which is a continuation of application No. 17/450,977, filed on Oct. 14, 2021, application No. 17/809,531, filed on Jun. 28, 2022 is a continuation-in-part of application No. 17/572,206, filed on Jan. 10, 2022, now Pat. No. 11,589,881, which is a continuation of application No.
(Continued)

(51) Int. Cl.
*A61B 17/22* (2006.01)
*A61B 17/221* (2006.01)
*A61B 17/00* (2006.01)
*A61M 25/10* (2013.01)

(52) U.S. Cl.
CPC ...... *A61B 17/22032* (2013.01); *A61B 17/221* (2013.01); *A61B 2017/00867* (2013.01); *A61B 2017/22038* (2013.01); *A61B 2017/22051* (2013.01); *A61B 2017/22054* (2013.01); *A61B 2017/22072* (2013.01); *A61B 2017/22079* (2013.01); *A61B 2017/22094* (2013.01); *A61M 2025/1013* (2013.01); *A61M 2025/1015* (2013.01)

(58) Field of Classification Search
CPC ............ A61B 17/22032; A61B 17/221; A61B 2017/00867; A61B 2017/22038; A61B 2017/22051; A61B 2017/22054; A61B 2017/22072; A61B 2017/22079; A61B 2017/22094; A61B 2017/00309; A61B 2017/320008; A61B 17/3207; A61B 2017/22068; A61B 2017/2212; A61B 2017/320733; A61M 2025/1013; A61M 2025/1015
See application file for complete search history.

(56) References Cited

U.S. PATENT DOCUMENTS

| 5,409,470 A | 4/1995 | McIntyre et al. |
| 2005/0020974 A1 | 1/2005 | Noriega et al. |

(Continued)

*Primary Examiner* — Richard G Louis
(74) *Attorney, Agent, or Firm* — Francis Law Group

(57) ABSTRACT

In various embodiments, the present specification discloses an aspiration catheter that has a slim profile, can effectively anchor or self-center in a location, within a patient's vessel lumen, to better provide directed suction or vacuum/negative pressure, and/or can effectively funnel or direct suction or vacuum/negative pressure toward an occlusion or obstruction within the patient's vessel lumen.

20 Claims, 22 Drawing Sheets

Related U.S. Application Data

17/450,978, filed on Oct. 14, 2021, now Pat. No. 12,114,877.

(60) Provisional application No. 63/215,573, filed on Jun. 28, 2021, provisional application No. 63/364,168, filed on May 4, 2022, provisional application No. 63/268,094, filed on Feb. 16, 2022, provisional application No. 63/260,406, filed on Aug. 19, 2021, provisional application No. 63/215,724, filed on Jun. 28, 2021, provisional application No. 63/215,579, filed on Jun. 28, 2021, provisional application No. 63/215,587, filed on Jun. 28, 2021, provisional application No. 63/215,583, filed on Jun. 28, 2021, provisional application No. 63/215,565, filed on Jun. 28, 2021, provisional application No. 63/092,428, filed on Oct. 15, 2020.

(56) References Cited

U.S. PATENT DOCUMENTS

| | | |
|---|---|---|
| 2005/0171592 A1 | 8/2005 | Majercak et al. |
| 2008/0058730 A1 | 3/2008 | Melsheimer |
| 2014/0058421 A1 | 2/2014 | Lupton et al. |

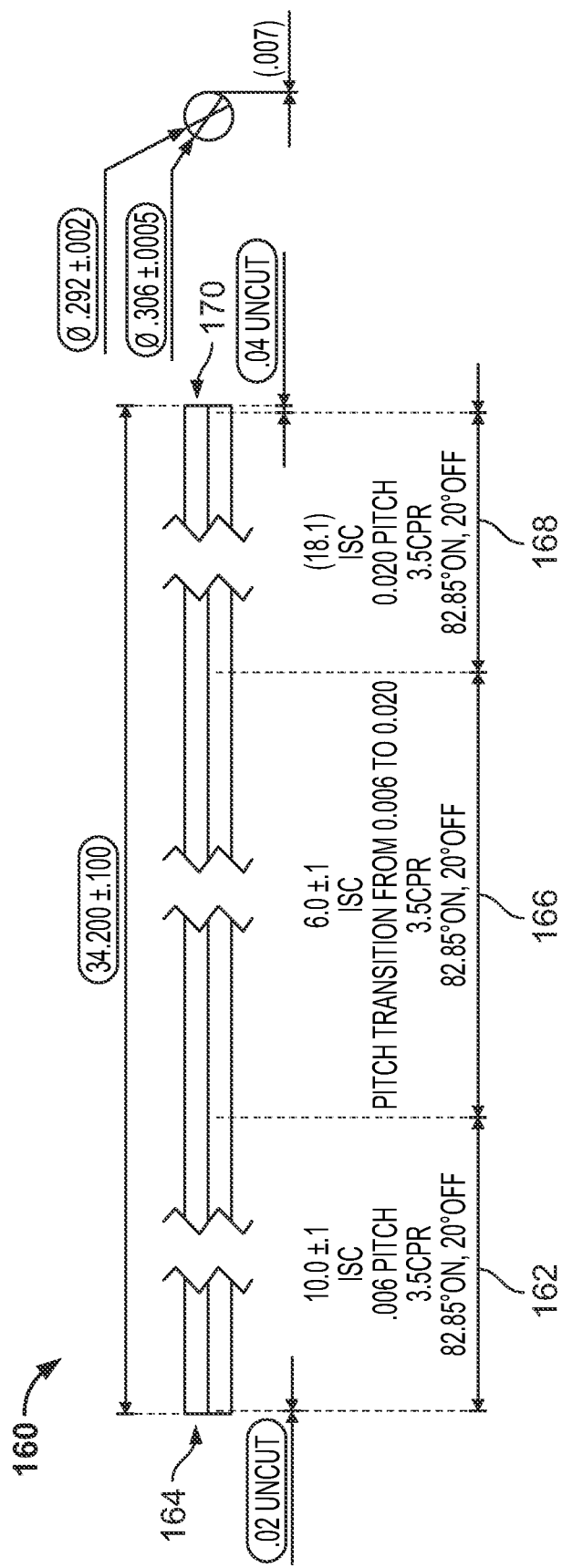

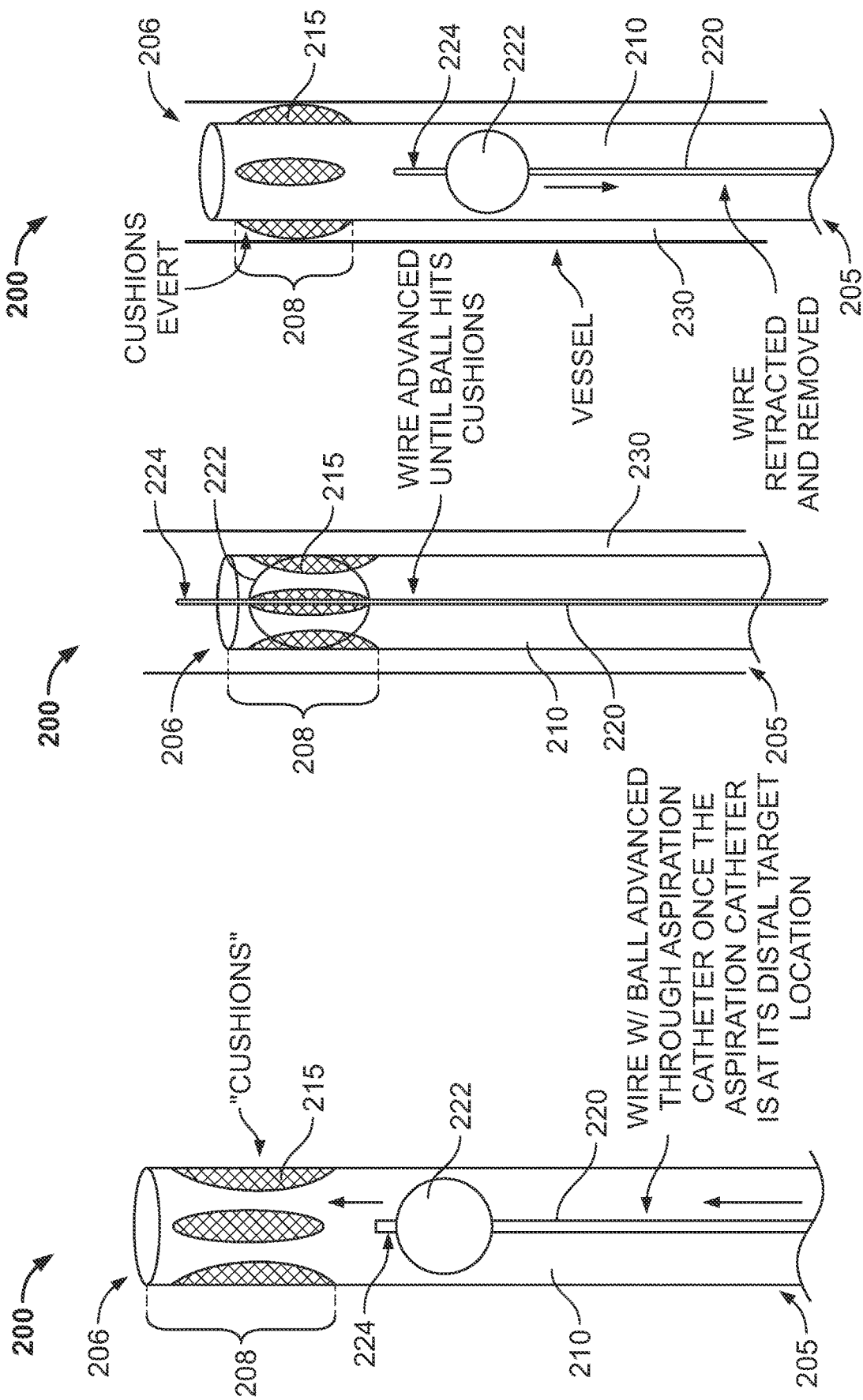

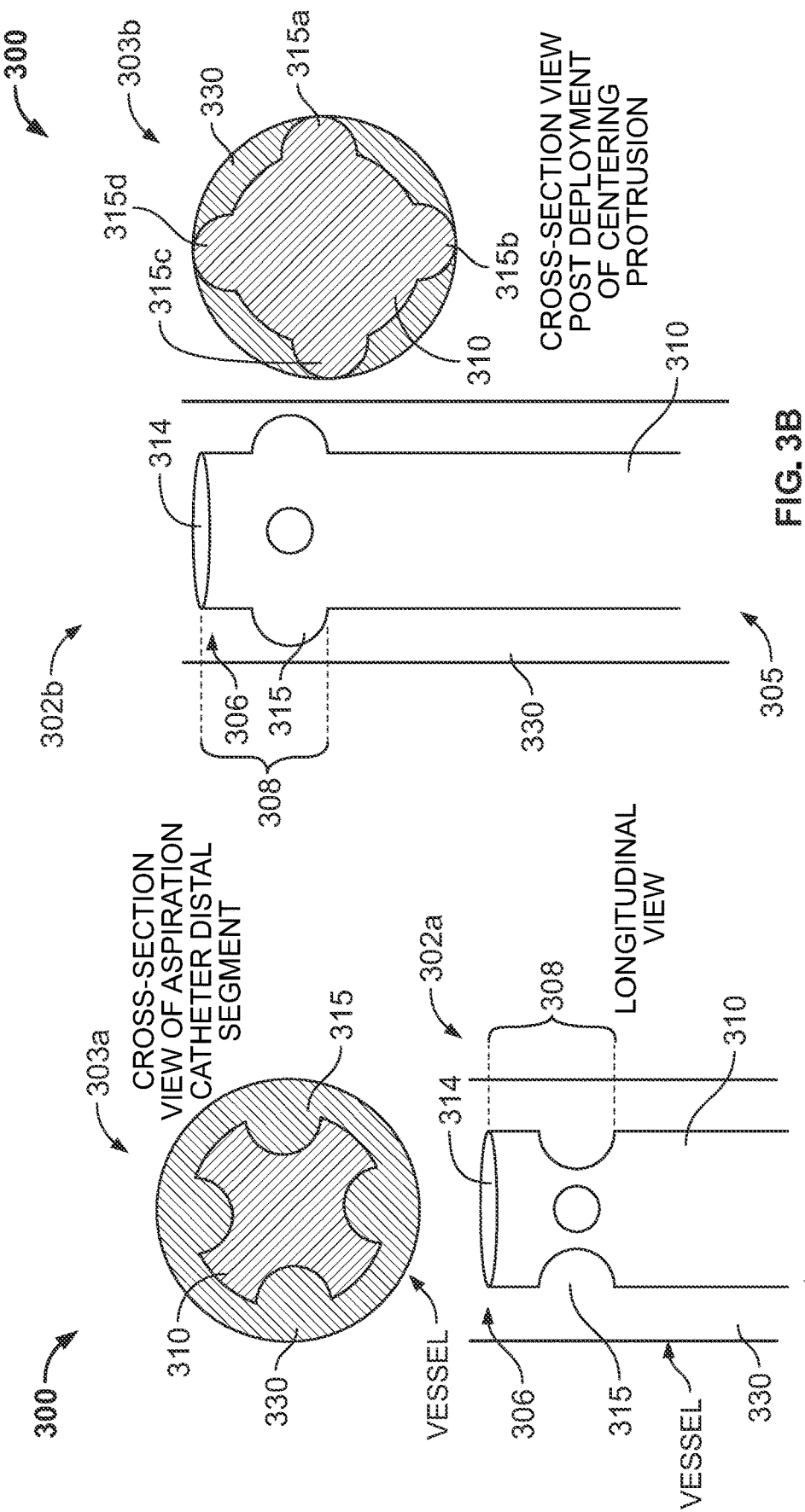

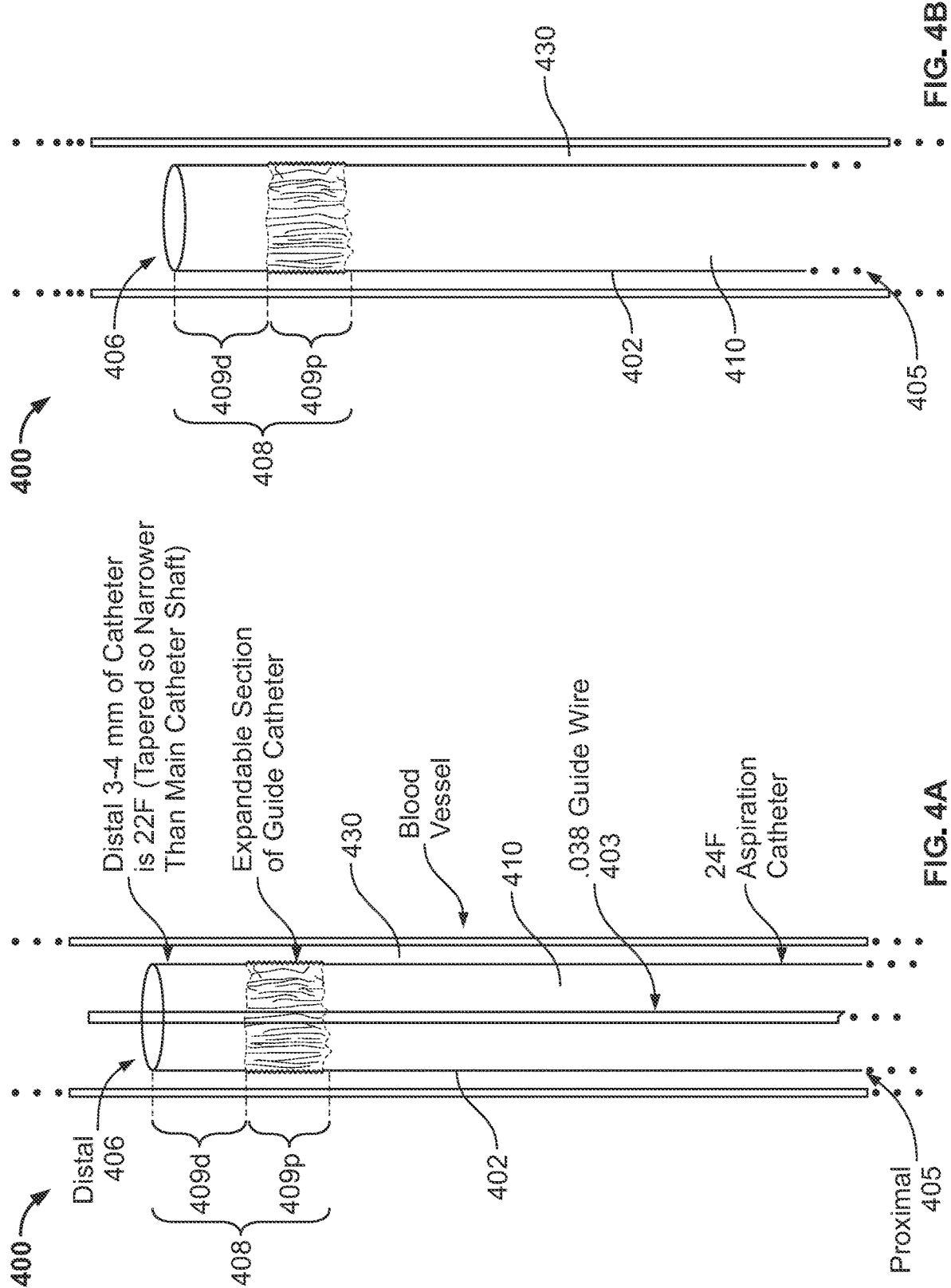

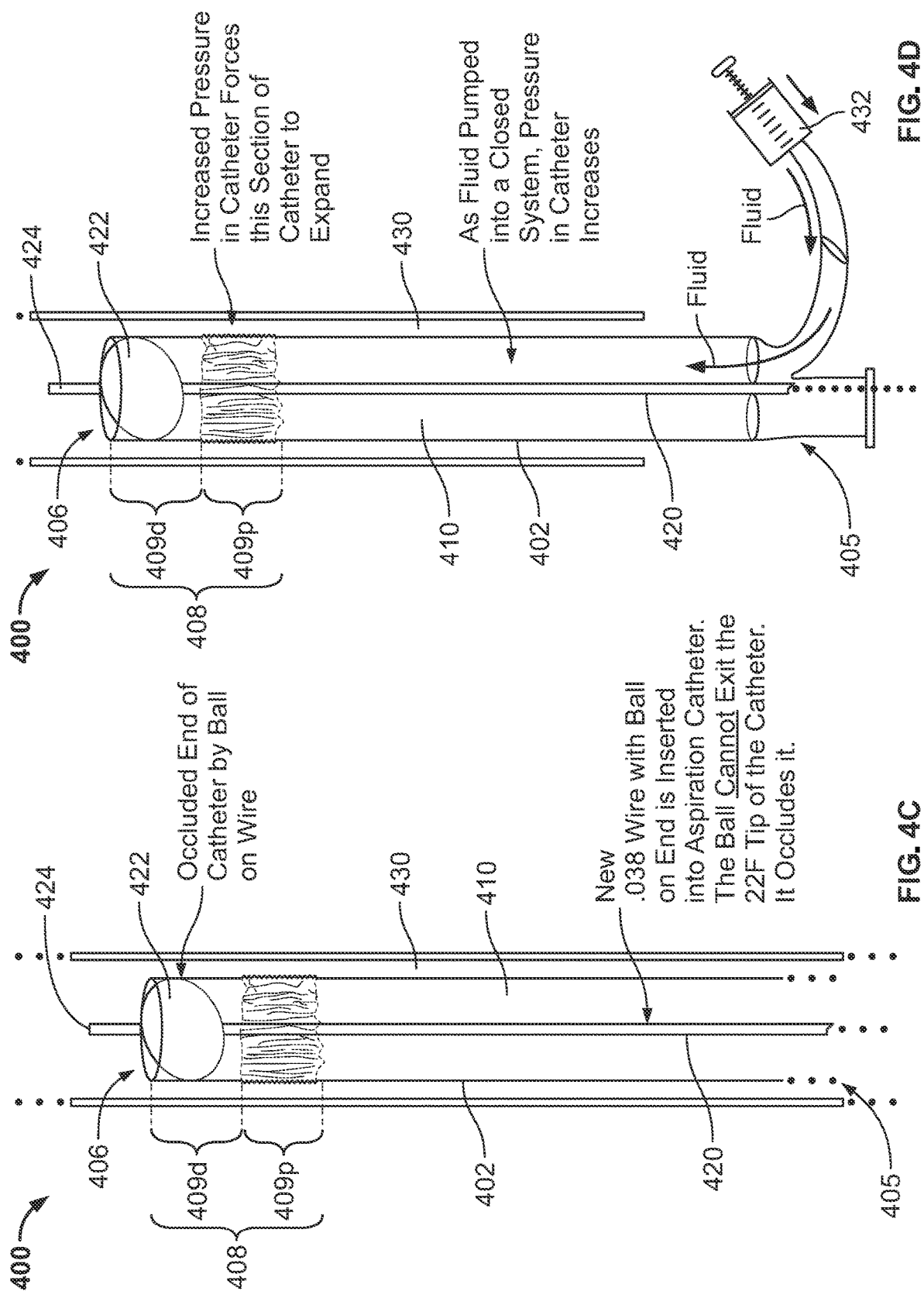

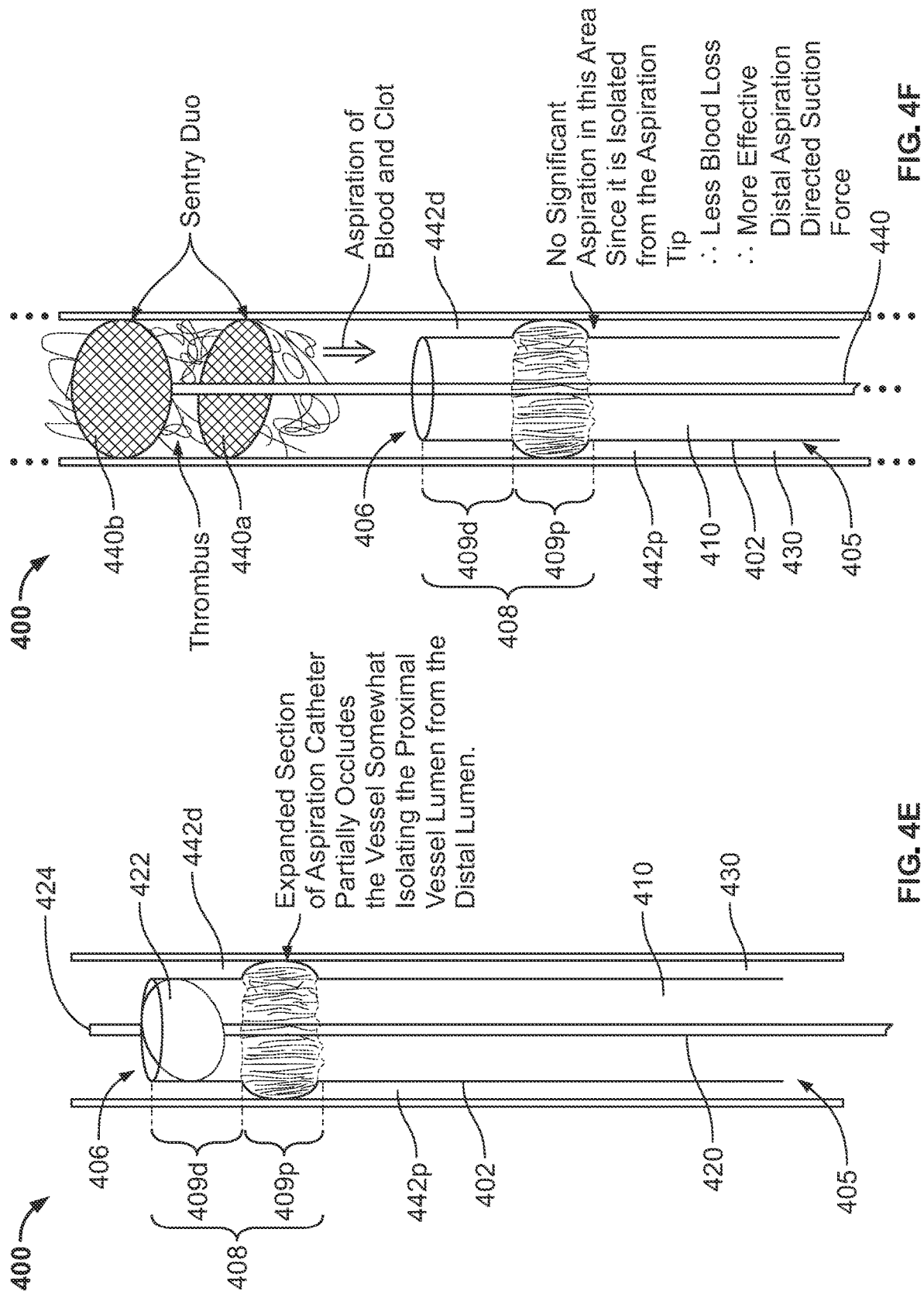

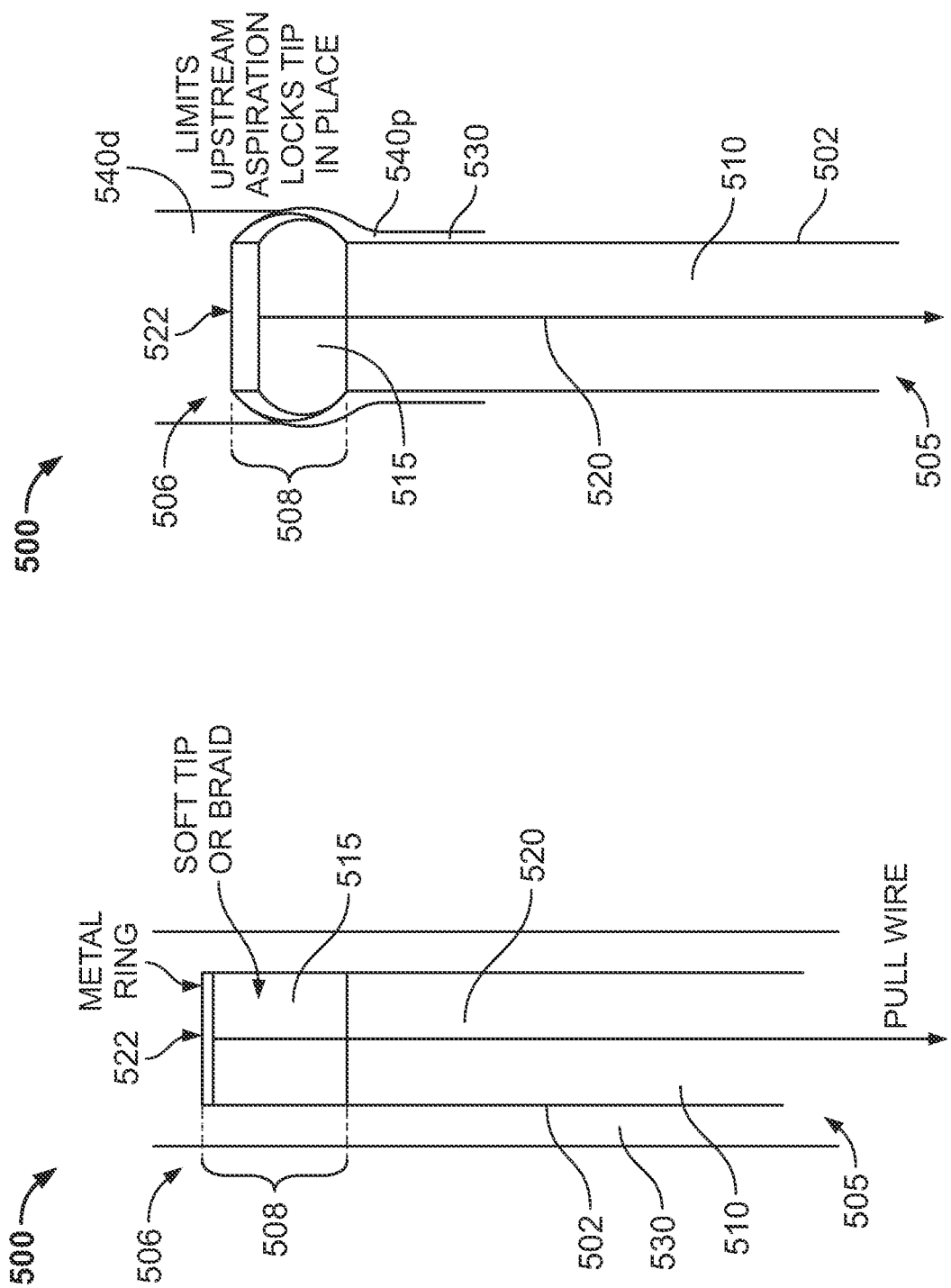

550 — An aspiration catheter is advanced into a patient's vessel lumen till a tip of the catheter is positioned proximate an occlusion within a patient's vessel lumen. At this stage, a restraining member restrains an expanding structure at the tip to be in the first state.

552 — A wire, attached to the restraining member, is pulled at its proximal end causing the restraining member to uncover the expanding structure thereby transitioning the structure, and therefore the tip, from the first state to a second state. The tip in the second state, contacts the inner walls of the patient's vessel lumen and enables the tip to be automatically centered in the vessel lumen

FIG. 5C

850 — An aspiration catheter is advanced into a patient's vessel lumen, over a guide wire, till a tip of the catheter is positioned proximate an occlusion within a patient's vessel lumen. An expandable structure is positioned on the tip, wherein the structure has a proximal portion, an intermediate portion in a first state and a distal portion 852 — The proximal end of the catheter is rotated or turned, in a first direction, causing a distal portion of the structure to translate proximally thereby transitioning the intermediate portion to a second state. The intermediate portion, in the second state, contacts the inner walls of the patient's vessel lumen enabling the tip to be centered in the vessel lumen 854 — A retriever device is advanced through the catheter lumen, during a thrombectomy procedure, to scrape, dislodge, break-up and capture the occlusion 856 — Suction, applied through the distal end of the catheter, is directed by the centered tip towards the occlusion thereby capturing the occlusion material (dislodged by the retriever device) and directing the occlusion material into the aspiration catheter 858 — The proximal end of the catheter is rotated or turned, in a second direction opposite to the first direction, causing the distal portion of the structure to translate distally thereby transitioning the intermediate portion from the second state to the first state 860 — The catheter and the retriever device are withdrawn from the vessel lumen

FIG. 8B

ASPIRATION CATHETERS AND METHODS OF USE THEREOF

CROSS-REFERENCE

The present application relies on U.S. Patent Provisional Application No. 63/215,573, titled "Aspiration Catheters and Methods of Use Thereof" and filed on Jun. 28, 2021, for priority. The above-mentioned application is herein incorporated by reference in its entirety.

The present application also relies on, for priority, U.S. Patent Provisional Application No. 63/364,168, titled "Clot Removal Methods and Devices with Specialized Clot Removal Elements" and filed on May 4, 2022, and U.S. Patent Provisional Application No. 63/268,094, titled "Methods and Devices for Removing and Filtering Clots to Isolate Blood for Reinfusion into a Patient" and filed on Feb. 16, 2022.

The present application is also a continuation-in-part application of U.S. patent application Ser. No. 17/572,138, titled "Clot Removal Methods and Devices with Multiple Independently Controllable Elements" and filed on Jan. 10, 2022, which is a continuation application of U.S. patent application Ser. No. 17/450,977, of the same title and filed on Oct. 14, 2021.

The present application is also a continuation-in-part application of U.S. patent application Ser. No. 17/572,206, titled "Clot Removal Methods and Devices with Multiple Independently Controllable Elements" and filed on Jan. 10, 2022, which is a continuation application of U.S. patent application Ser. No. 17/450,978, of the same title and filed on Oct. 14, 2021.

Both U.S. patent application Ser. No. 17/450,977 and U.S. patent application Ser. No. 17/450,978 rely on, for priority, the following provisional applications:

U.S. Patent Provisional Application No. 63/260,406, titled "Catheter Based Retrieval Device" and filed on Aug. 19, 2021;

U.S. Patent Provisional Application No. 63/215,724, titled "Device and Method of Using the Device for Repairing A Pathological Connection Between Two Anatomical Structures" and filed on Jun. 28, 2021;

U.S. Patent Provisional Application No. 63/215,579, titled "Hub and Valve Systems for an Aspiration Catheter" and filed on Jun. 28, 2021;

U.S. Patent Provisional Application No. 63/215,573, titled "Aspiration Catheters and Methods of Use Thereof" and filed on Jun. 28, 2021;

U.S. Patent Provisional Application No. 63/215,587, titled "Vascular Closure Devices and Methods of Using Thereof" and filed on Jun. 28, 2021;

U.S. Patent Provisional Application No. 63/215,583, titled "Catheters with Expandable and Collapsible Lumens" and filed on Jun. 28, 2021;

U.S. Patent Provisional Application No. 63/215,565, titled "Catheter Based Retrieval Device" and filed on Jun. 28, 2021; and U.S. Patent Provisional Application No. 63/092,428, titled "Catheter Based Retrieval Device with Proximal Body Having Axial Freedom of Movement" and filed on Oct. 15, 2020.

All of the above-mentioned patents and applications are hereby incorporated by reference in their entirety.

FIELD

The present specification relates generally to aspiration catheters. More particularly, the present specification relates to aspiration catheters that direct suction substantially towards occlusion material within a patient's vessel lumen and not towards the vessel wall or other freely flowing blood.

BACKGROUND

Many medical procedures, such as, for example, mechanical thrombectomy, involve introduction of at least one medical instrument into arterial, venous and neural systems so that the medical instrument may be advanced to a body location requiring diagnosis or treatment. For example, a guide catheter may be advanced through a patient's vasculature (such as those in the brain) to a desired treatment location and the medical instrument advanced through the guide catheter for the removal of occlusions, such as thrombi.

The guide catheter is often inserted through an aspiration catheter which is then used to purge occlusion material removed by the medical instrument from the treatment location. For effective aspiration of the occlusion material it is highly desirable that suction, applied through a tip of the aspiration catheter, be directed towards the occlusion and not towards the vessel wall or other freely flowing blood.

Accordingly, there exists a need for an aspiration catheter whose tip may be substantially centered within a patient's vessel lumen so that negative pressure through the tip may be directed substantially towards the occlusion material.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses an aspiration catheter having a proximal end, a distal end and a lumen extending between the proximal end and the distal end and configured to receive a second catheter, wherein the distal end comprises: a proximal portion, wherein the proximal portion comprises a first solid material defining a first hollow, enclosed tube; a distal portion, wherein the distal portion comprises a second solid material defining a second hollow, enclosed tube, wherein the distal portion is configured to move in a proximal direction and a distal direction along a longitudinal axis of the distal end, and wherein an inner surface of the distal portion comprises a first plurality of threads configured to engage with a second plurality of threads formed on an outer surface of a distal end of the second catheter; and an intermediate portion coupled to and extending between the proximal portion and the distal portion, wherein the intermediate portion comprises a flexible material that is different than the first solid material and the second solid material, wherein the intermediate portion has at least a first state and a second state, and wherein movement of the proximal end in a first direction causes the distal portion to translate proximally, thereby transitioning the intermediate portion to the second state, and wherein movement of the proximal end in a second direction, opposite to the first direction, causes the distal portion to translate distally thereby transitioning the intermediate portion to the first state.

Optionally, the first solid material is one or a combination of the following materials: PTFE, urethane, nylon, stainless steel, nitinol, polyimide, and/or polyethylene terephthalate (PET) and the second solid material is one or a combination of the following materials: stainless steel, nitinol, nylon, and/or PEEK.

Optionally, the first state corresponds to the intermediate portion being in a substantially linear, non-expanded configuration.

Optionally, the second state corresponds to the intermediate portion being in an expanded configuration and wherein, in the expanded configuration, the intermediate portion acquires a substantially spherical, cylindrical, or elliptical shape in the second state.

Optionally, the intermediate portion is a mesh of braided wires.

Optionally, the movement of the proximal end in the first direction or second direction is a rotation of the proximal end.

Optionally, a length of each of the first plurality of threads and the second plurality of threads is in a range of 3 mm to 40 mm.

Optionally, the inner surface of the distal portion comprises a first plurality of threads configured to engage with a second plurality of threads formed on the outer surface of the distal end of the second catheter. Optionally, rotation of the proximal end in the first direction causes the distal portion to translate proximally via the engagement of the first plurality of threads and the second plurality of threads, thereby transitioning the intermediate portion to the second state. Optionally, rotation of the proximal end in the second direction, opposite to the first direction, causes the distal portion to translate distally via the engagement of the first plurality of threads and the second plurality of threads, thereby transitioning the intermediate portion to the first state.

The present specification also discloses a method of centering a tip of an aspiration catheter within a patient's vessel lumen, said aspiration catheter having a proximal end, a distal end, and a lumen extending between the proximal end and the distal end and configured to receive a second catheter, said tip being proximate the distal end, wherein a structure is positioned at the tip, said structure having a proximal portion, an intermediate portion, and a distal portion, wherein the proximal portion is fixed, the intermediate portion is coupled to and extends between the proximal portion and distal portion and is in a first state and the distal portion is free to move in proximal and distal directions along a longitudinal axis of the distal end of the aspiration catheter, and wherein an inner surface of the distal portion has a first plurality of threads configured to engage with a second plurality of threads formed on an outer surface of a distal end of the second catheter, the method comprising: positioning the tip proximate an occlusion within the vessel lumen; moving the proximal end of the catheter in a first direction to translate the distal portion of the structure proximally thereby transitioning the intermediate portion to a second state, wherein the intermediate portion in the second state contacts inner walls of the vessel lumen enabling the tip to be centered in the vessel lumen; advancing a device into the catheter lumen and through the opening for dislodging the occlusion; and applying suction through the distal end of the catheter, wherein the centered tip directs said suction towards the occlusion thereby capturing and directing the occlusion into the catheter.

Optionally, the method further comprises: moving the proximal end in a second direction opposite to the first direction to translate the distal portion distally thereby transitioning the intermediate portion to the first state; and withdrawing the catheter and the device from the vessel lumen.

Optionally, the proximal and distal portions are hollow tubes encompassing the tip.

Optionally, the first state corresponds to the intermediate portion being in a substantially linear, non-expanded configuration.

Optionally, the second state corresponds to the intermediate portion being in an expanded configuration wherein, in the expanded configuration, the intermediate portion acquires a substantially spherical, cylindrical, or elliptical shape in the second state.

Optionally, the intermediate portion is a mesh of braided wires.

Optionally, the movement of the proximal end in the first direction or second direction is a rotation of the proximal end.

Optionally, a length of each of the first plurality of threads and of the second plurality of threads is in a range of 3 mm to 40 mm.

Optionally, movement of the proximal end in the first direction causes the distal portion to translate proximally via the engagement of the first plurality of threads and the second plurality of threads, thereby transitioning the intermediate portion to the second state.

Optionally, movement of the proximal end in the second direction, opposite to the first direction, causes the distal portion to translate distally via the engagement of the first plurality of threads and the second plurality of threads, thereby transitioning the intermediate portion to the first state.

In some embodiments, the present specification discloses an aspiration catheter having a proximal end, a distal end and a catheter lumen leading to an opening at the distal end, comprising: a plurality of members at a tip proximate the distal end, wherein each of the plurality of members is positioned within a cavity, and wherein each of the plurality of members is in a first configuration; and a wire having a shaped element at a distal end of the wire, wherein when the tip is positioned within a vessel lumen the wire is advanced into the catheter lumen until the shaped element hits the plurality members and causes each of the plurality of members to be transitioned to a second configuration.

Optionally, the first configuration corresponds to each of the plurality of members protruding into the catheter lumen.

Optionally, the second configuration corresponds to each of the plurality of members protruding into the vessel lumen.

Optionally, each of the plurality of members is a tightly woven mesh of Nitinol.

Optionally, each of the plurality of members has a substantially quadrangular or hemispherical shape.

Optionally, the plurality of members in the second configuration contact inner walls of the vessel lumen and enable the tip to be cantered in the vessel lumen.

Optionally, the plurality of members includes first, second, third and fourth members, wherein the first and second members are positioned diametrically opposite to each other, the third and fourth members are positioned diametrically opposite to each other, and the first, second, third and fourth members are separated by an angle of 90 degrees from each other around a circular cross-section of the catheter lumen.

In some embodiments, the present specification discloses a method of centering a tip of an aspiration catheter within a patient's vessel lumen, said aspiration catheter having a proximal end, a distal end and a catheter lumen leading to an opening at the distal end, and said tip being proximate the distal end, wherein the tip includes a plurality of members, and wherein each of said plurality of members is in a first configuration, the method comprising: positioning the tip proximate an occlusion within the vessel lumen; and advancing, through the catheter lumen, a wire having a shaped element at a distal end of the wire until the shaped element hits the plurality members, wherein the shaped element causes each of the plurality of members to transition to a second configuration.

Optionally, the first configuration corresponds to each of the plurality of members protruding into the catheter lumen.

Optionally, the second configuration corresponds to each of the plurality of members protruding into the vessel lumen.

Optionally, each of the plurality of members is a tightly woven mesh of Nitinol.

Optionally, each of the plurality of members has a substantially quadrangular or hemispherical shape.

Optionally, the plurality of members in the second configuration contact inner walls of the vessel lumen and enable the tip to be cantered in the vessel lumen.

Optionally, the plurality of members includes first, second, third and fourth members, wherein the first and second members are positioned diametrically opposite to each other, the third and fourth members are positioned diametrically opposite to each other, and the first, second, third and fourth members are separated by an angle of 90 degrees from each other around a circular cross-section of the catheter lumen.

In some embodiments, the present specification discloses an aspiration catheter having a proximal end, a distal end and a catheter lumen leading to an opening at the distal end, comprising: a cap occluding the opening at the distal end; a plurality of members at a tip proximate the distal end, wherein each of the plurality of members is positioned within a cavity, and wherein each of the plurality of members is in a first configuration; and an indeflator coupled to the proximal end, wherein when the tip is positioned within a patient's vessel lumen the indeflator is actuated to pump a fluid into the catheter lumen thereby raising pressure within the catheter lumen, and wherein the raised pressure causes each of the plurality of members to be transitioned to a second configuration.

Optionally, the first configuration corresponds to each of the plurality of members protruding into the catheter lumen.

Optionally, the second configuration corresponds to each of the plurality of members protruding into the vessel lumen.

Optionally, each of the plurality of members is a tightly woven mesh of Nitinol.

Optionally, each of the plurality of members has a substantially quadrangular or hemispherical shape.

Optionally, the plurality of members in the second configuration contact inner walls of the vessel lumen and enable the tip to be cantered in the vessel lumen.

Optionally, the plurality of members includes first, second, third and fourth members, wherein the first and second members are positioned diametrically opposite to each other, the third and fourth members are positioned diametrically opposite to each other, and the first, second, third and fourth members are separated by an angle of 90 degrees from each other around a circular cross-section of the catheter lumen.

Optionally, the cap ruptures when said pressure within the catheter lumen reaches a predefined threshold value.

In some embodiments, the present specification discloses a method of centering a tip of an aspiration catheter within a patient's vessel lumen, said aspiration catheter having a proximal end, a distal end and a catheter lumen leading to an opening at the distal end, said opening being occluded by a cap and said tip being proximate the distal end, wherein the tip includes a plurality of members, and wherein each of said plurality of members is in a first configuration, the method comprising: positioning the tip proximate an occlusion within the vessel lumen; and pumping a fluid through the proximal end into the catheter lumen thereby raising pressure within the catheter lumen, wherein the raised pressure causes each of the plurality of members to transition to a second configuration.

Optionally, the first configuration corresponds to each of the plurality of members protruding into the catheter lumen.

Optionally, the second configuration corresponds to each of the plurality of members protruding into the vessel lumen.

Optionally, each of the plurality of members is a tightly woven mesh of Nitinol.

Optionally, each of the plurality of members has a substantially quadrangular or hemispherical shape.

Optionally, the plurality of members in the second configuration contact inner walls of the vessel lumen and enable the tip to be cantered in the vessel lumen.

Optionally, the plurality of members includes first, second, third and fourth members, wherein the first and second members are positioned diametrically opposite to each other, the third and fourth members are positioned diametrically opposite to each other, and the first, second, third and fourth members are separated by an angle of 90 degrees from each other around a circular cross-section of the catheter lumen.

Optionally, the cap ruptures when said pressure within the catheter lumen reaches a predefined threshold value.

In some embodiments, the present specification discloses an aspiration catheter having a proximal end, a distal end and a catheter lumen leading to an opening at the distal end, comprising: a tip proximate the distal end, wherein the tip has a proximal portion and a distal portion, said proximal portion having a first outer diameter and a first state, and wherein the distal portion tapers from the first outer diameter to a second outer diameter towards the opening; and a wire having a shaped element at a distal end of the wire, wherein when the tip is positioned within a patient's vessel lumen the wire is advanced into the catheter lumen until the shaped element occludes the opening, and wherein a fluid is pumped into the catheter lumen with the occluded opening thereby raising pressure within the catheter lumen and causing the proximal portion to transition to a second state.

Optionally, the first state corresponds to the proximal portion being in a non-dilated configuration.

Optionally, the second state corresponds to the proximal portion being in a dilated configuration.

Optionally, the proximal portion has a third outer diameter in the second state, and wherein the third outer diameter is greater than the first outer diameter.

Optionally, the second outer diameter is less than the first outer diameter, and wherein an outer diameter of the shaped element is less than the first diameter but greater than the second diameter.

Optionally, the wire is retracted and removed from the catheter lumen after the proximal portion transitions to the second configuration.

Optionally, walls of the proximal portion are formed of foldable material and/or thin collapsible foils.

Optionally, the proximal portion in the second state contacts inner walls of the vessel lumen and enables the tip to be cantered in the vessel lumen.

In some embodiments, the present specification discloses a method of centering a tip of an aspiration catheter within a patient's vessel lumen, said aspiration catheter having a proximal end, a distal end and a catheter lumen leading to an opening at the distal end, said tip being proximate the distal end, wherein the tip has a proximal portion and a distal portion, wherein the proximal portion has a first outer diameter and a first state, and wherein the distal portion tapers from the first outer diameter to a second outer diameter towards the opening, the method comprising: positioning the tip proximate an occlusion within the vessel lumen; advancing, through the catheter lumen, a wire having a shaped element at a distal end of the wire until the shaped element occludes the opening at the distal end; and pumping a fluid through the proximal end into the catheter lumen thereby raising pressure within the catheter lumen, wherein the raised pressure causes the proximal portion to transition to a second configuration.

Optionally, the first state corresponds to the proximal portion being in a non-dilated configuration.

Optionally, the second state corresponds to the proximal portion being in a dilated configuration.

Optionally, the proximal portion has a third outer diameter in the second state, and wherein the third outer diameter is greater than the first outer diameter.

Optionally, the second outer diameter is less than the first outer diameter, and wherein an outer diameter of the shaped element is less than the first diameter but greater than the second diameter.

Optionally, the wire is retracted and removed from the catheter lumen after the proximal portion transitions to the second configuration.

Optionally, walls of the proximal portion are formed of foldable material and/or thin collapsible foils.

Optionally, the proximal portion in the second state contacts inner walls of the vessel lumen and enables the tip to be cantered in the vessel lumen.

In some embodiments, the present specification discloses an aspiration catheter having a proximal end, a distal end and a catheter lumen leading to an opening at the distal end, comprising: a structure positioned at a tip proximate the distal end; a member positioned at the distal end, wherein the member encompasses the structure thereby restraining the structure in a first state; and a wire having a proximal end and a distal end, wherein the distal end of the wire is attached to the member so that the wire extends from the member to the proximal end of the catheter within the catheter lumen, wherein when the tip is positioned within a patient's vessel lumen the proximal end of the wire is pulled causing the member to collapse into the catheter lumen and releasing the structure, and wherein said releasing causes the structure to transition to a second state.

Optionally, the first state corresponds to the structure being in a non-expanded configuration.

Optionally, the second state corresponds to the structure being in an expanded configuration.

Optionally, the structure is a self-expanding balloon, stent or mesh of braided wires.

Optionally, the member is configured as a cap or a ring.

Optionally, the structure has a substantially spherical or elliptical shape in the second state.

Optionally, the structure in the second state contacts inner walls of the vessel lumen and enables the tip to be cantered in the vessel lumen.

In some embodiments, the present specification discloses a method of centering a tip of an aspiration catheter within a patient's vessel lumen, said aspiration catheter having a proximal end, a distal end and a catheter lumen leading to an opening at the distal end, said tip being proximate the distal end, wherein the tip has a structure restrained in a first state by a member, and wherein a wire is attached to the member so that the wire extends from the member to the proximal end of the catheter within the catheter lumen, the method comprising: positioning the tip proximate an occlusion within the vessel lumen; and pulling a proximal end of the wire to collapse the member into the catheter lumen and release the structure, wherein said releasing causes the structure to transition to a second state.

Optionally, the first state corresponds to the structure being in a non-expanded configuration.

Optionally, the second state corresponds to the structure being in an expanded configuration.

Optionally, the structure is a self-expanding balloon, stent or mesh of braided wires.

Optionally, the member is configured as a cap or a ring.

Optionally, the structure has a substantially spherical or elliptical shape in the second state.

Optionally, the structure in the second state contacts inner walls of the vessel lumen and enables the tip to be cantered in the vessel lumen.

In some embodiments, the present specification discloses an aspiration catheter having a proximal end, a distal end and a catheter lumen leading to an opening at the distal end, comprising: a tip proximate the distal end; a wire positioned within the catheter lumen, wherein the wire has a proximal end and a distal end; and a plurality of braided wires, wherein each of the plurality of braided wires has a first end and a second end, wherein the first end is attached to the distal end of the catheter and the second end is attached to the distal end of the wire, and wherein to and fro (back and forth) reciprocating movement of the wire along a longitudinal axis of the catheter causes the second end to move thereby changing a collective configuration of the plurality of braided wires.

Optionally, suction is applied through the distal end concurrent to said reciprocating movement.

In some embodiments, the present specification discloses a method of applying suction through an aspiration catheter within a patient's vessel lumen, said aspiration catheter having a proximal end, a distal end and a catheter lumen leading to an opening at the distal end, wherein a wire is positioned within the catheter lumen, and wherein first ends of a plurality of braided wires are attached to the distal end and second ends of the plurality of braided wires are attached to a distal end of the wire, the method comprising: positioning the tip proximate an occlusion within the vessel lumen; moving the wire to and fro (back and forth) along a longitudinal axis of the catheter causes the second end to move thereby changing a collective configuration of the plurality of braided wires and breaking the occlusion; and applying suction through the distal end of the catheter in order to aspirate the broken occlusion.

Optionally, said suction is applied concurrent to said to and fro (back and forth) movement of the wire.

In some embodiments, the present specification discloses an aspiration catheter having a proximal end, a distal end and a catheter lumen leading to an opening at the distal end, comprising: a tip proximate the distal end of the catheter; and a structure attached to the opening, wherein a lumen extends from a proximal end to a distal end of the structure, wherein the structure has a proximal portion and a distal portion, wherein the structure is at least partially covered, and wherein when the tip is positioned proximate an occlusion within a patient's vessel lumen the structure directs suction applied through the distal end of the catheter substantially towards the occlusion.

Optionally, the proximal portion has a substantially conical shape and a first apex, wherein the distal portion has a substantially conical shape and a second apex, and wherein the first and second apexes point in opposite directions.

Optionally, the proximal portion is covered.

Optionally, a device is advanced into the catheter lumen and through the lumen in the structure for removing the occlusion.

In some embodiments, the present specification discloses a method of applying suction through an aspiration catheter within a patient's vessel lumen, said aspiration catheter having a proximal end, a distal end and a catheter lumen leading to an opening at the distal end, said catheter having a tip proximate the distal end of the catheter, wherein a structure is attached to the opening, wherein a lumen extends from a proximal end to a distal end of the structure, and wherein the structure has a proximal portion and a distal portion, the method comprising: positioning the tip proximate an occlusion within the vessel lumen; advancing a device into the catheter lumen and through the lumen in the structure for removing the occlusion; using the device to dislodge and break the occlusion; and applying suction through the distal end of the catheter, wherein the structure directs the suction substantially towards the occlusion in order to aspirate the occlusion into the catheter.

Optionally, the proximal portion has a substantially conical shape and a first apex, wherein the distal portion has a substantially conical shape and a second apex, and wherein the first and second apexes point in opposite directions.

Optionally, the proximal portion is covered.

In some embodiments, the present specification discloses an aspiration catheter having a proximal end, a distal end and a catheter lumen leading to an opening at the distal end, comprising: a tip proximate the distal end of the catheter; and a structure positioned on the tip, said structure having a proximal portion, an intermediate portion and a distal portion, wherein the proximal portion is fixed, the intermediate portion is in a first state and the distal portion is free to move in proximal and distal directions along a longitudinal axis of the catheter, wherein an inner surface of the distal portion has a first plurality of threads that engage with a second plurality of threads formed on an outer surface of the tip at the distal end, and wherein rotation of the proximal end in a first direction causes the distal portion to translate proximally thereby transitioning the intermediate portion to a second state whereas rotation of the proximal end in a second direction, opposite to the first direction, causes the distal portion to translate distally thereby transitioning the intermediate portion to the first state.

Optionally, the proximal and distal portions are hollow tubes encompassing the tip.

Optionally, the first state corresponds to the intermediate portion being in a non-expanded configuration.

Optionally, the second state corresponds to the intermediate portion being in an expanded configuration.

Optionally, the intermediate portion acquires a substantially spherical or elliptical shape in the second state.

Optionally, the intermediate portion acquires a substantially cylindrical shape around the tip in the first state.

Optionally, the intermediate portion is a tightly woven mesh of a plurality of braided wires.

Optionally, the intermediate portion, in the second state, contacts inner walls of a patient's vessel lumen enabling the tip to be centered in the vessel lumen.

In some embodiments, the present specification discloses a method of centering a tip of an aspiration catheter within a patient's vessel lumen, said aspiration catheter having a proximal end, a distal end and a catheter lumen leading to an opening at the distal end, said tip being proximate the distal end, wherein a structure is portioned at the tip, said structure having a proximal portion, an intermediate portion and a distal portion, wherein the proximal portion is fixed, the intermediate portion is in a first state and the distal portion is free to move in proximal and distal directions along a longitudinal axis of the catheter, and wherein an inner surface of the distal portion has a first plurality of threads that engage with a second plurality of threads formed on an outer surface of the tip at the distal end, the method comprising: positioning the tip proximate an occlusion within the vessel lumen; rotating the proximal end in a first direction to translate the distal portion proximally thereby transitioning the intermediate portion to a second state, wherein the intermediate portion in the second state contacts inner walls of the vessel lumen enabling the tip to be centered in the vessel lumen; advancing a device into the catheter lumen and through the opening for dislodging the occlusion; and applying suction through the distal end, wherein the centered tip directs said suction towards the occlusion thereby capturing and directing the occlusion into the catheter.

Optionally, the method further comprises rotating the proximal end in a second direction opposite to the first direction to translate the distal portion distally thereby transitioning the intermediate portion to the first state; and withdrawing the catheter and the device from the vessel lumen.

Optionally, the proximal and distal portions are hollow tubes encompassing the tip.

Optionally, the first state corresponds to the intermediate portion being in a non-expanded configuration.

Optionally, the second state corresponds to the intermediate portion being in an expanded configuration.

Optionally, the intermediate portion acquires a substantially spherical or elliptical shape in the second state.

Optionally, the intermediate portion acquires a substantially cylindrical shape around the tip in the first state.

Optionally, the intermediate portion is a tightly woven mesh of a plurality of braided wires.

Optionally, the intermediate portion, in the second state, contacts inner walls of a patient's vessel lumen enabling the tip to be centered in the vessel lumen.

In some embodiments, the present specification discloses an aspiration catheter having a proximal end and a distal end, the catheter being in a first state, comprising: a tip proximate the distal end; a first lumen leading to a first opening at the distal end and a second lumen leading to a second opening at the distal end; and a member occluding the first lumen, wherein a fluid is pumped into the first lumen thereby raising pressure within the first lumen and causing the catheter to transition to a second state.

Optionally, the member is configured as a cap or a plug.

Optionally, the first state corresponds to the catheter being in a non-dilated state.

Optionally, the second state corresponds to the catheter being in a dilated state.

Optionally, the catheter has a first outer diameter in the first state and a second outer diameter in the second state, and wherein the second outer diameter is greater than the first outer diameter.

Optionally, walls of the catheter are formed using foldable material and/or thin collapsible foils.

Optionally, the tip includes a plurality of scrapers.

Optionally, the member ruptures when said pressure within the first lumen reaches a predefined threshold value.

In some embodiments, the present specification discloses a method of using an aspiration catheter within a patient's vessel lumen, said aspiration catheter having a proximal end, a distal end, a first lumen leading to a first opening at the distal end, a second lumen leading to a second opening at the distal end, and a tip proximate the distal end, wherein the first lumen is occluded by a member, and wherein the catheter is in a first state, the method comprising: positioning the tip proximate an occlusion within the vessel lumen; pumping a fluid through the proximal end into the first lumen thereby raising pressure within the first lumen, wherein the raised pressure causes the catheter to transition to a second state; and moving the catheter axially to and fro (back and forth) within the vessel lumen, wherein said movement causes a plurality of scrapers, positioned on the tip, to scrape and pull out the occlusion from within the vessel lumen.

Optionally, the member is configured as a cap or a plug.

Optionally, the first state corresponds to the catheter being in a non-dilated state.

Optionally, the second state corresponds to the catheter being in a dilated state.

Optionally, the catheter has a first outer diameter in the first state and a second outer diameter in the second state, and wherein the second outer diameter is greater than the first outer diameter.

Optionally, walls of the catheter are formed using foldable material and/or thin collapsible foils.

Optionally, the member ruptures when said pressure within the first lumen reaches a predefined threshold value.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 1B illustrates a schematic view of the middle layer of aspiration catheter, in accordance with some embodiments of the present specification;

FIG. 2B illustrates a wire with a ball-shaped element being advanced into a lumen of the aspiration catheter of FIG. 2A, in accordance with some embodiments of the present specification;

FIG. 2C illustrates the wire with the ball-shaped element hitting a plurality of centering members of the aspiration catheter of FIG. 2A, in accordance with some embodiments of the present specification;

FIG. 2D illustrates the wire with the ball-shaped element being removed from of the aspiration catheter of FIG. 2A, in accordance with some embodiments of the present specification;

FIG. 3A illustrates a longitudinal view and a transverse cross-sectional view of an aspiration catheter in a first configuration, in accordance with some embodiments of the present specification;

FIG. 3B illustrates a longitudinal view and a transverse cross-sectional view of the aspiration catheter of FIG. 3A in a second configuration, in accordance with some embodiments of the present specification;

FIG. 4A illustrates a longitudinal view of an aspiration catheter (in a first state) being positioned within a patient's vessel lumen using a guide wire, in accordance with some embodiments of the present specification;

FIG. 4B illustrates the aspiration catheter of FIG. 4A positioned within the patient's vessel lumen and the guide wire removed, in accordance with some embodiments of the present specification;

FIG. 4C illustrates a wire with a ball-shaped element occluding an opening at a distal end of the aspiration catheter of FIG. 4A, in accordance with some embodiments of the present specification;

FIG. 4D illustrates a fluid being pumped into a lumen of the aspiration catheter of FIG. 4A, in accordance with some embodiments of the present specification;

FIG. 4E illustrates the aspiration catheter of FIG. 4A in a second state, in accordance with some embodiments of the present specification;

FIG. 4F illustrates a retriever device being advanced into the lumen of the aspiration catheter of FIG. 4A, in accordance with some embodiments of the present specification;

FIG. 5A illustrates a longitudinal view of an aspiration catheter in a first state, in accordance with some embodiments of the present specification;

FIG. 5B illustrates the aspiration catheter of FIG. 5A in a second state, in accordance with some embodiments of the present specification;

FIG. 5C is a flowchart of a plurality of exemplary steps of a method of centering the aspiration catheter of FIG. 5A within a patient's vessel lumen, in accordance with some embodiments of the present specification;

FIG. 8B is a flowchart of a plurality of exemplary steps of a method of centering the aspiration catheter of FIG. 8A within a patient's vessel lumen, in accordance with some embodiments of the present specification;

DETAILED DESCRIPTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise", "include", "have", "contain", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

Overview

Figure 1A:
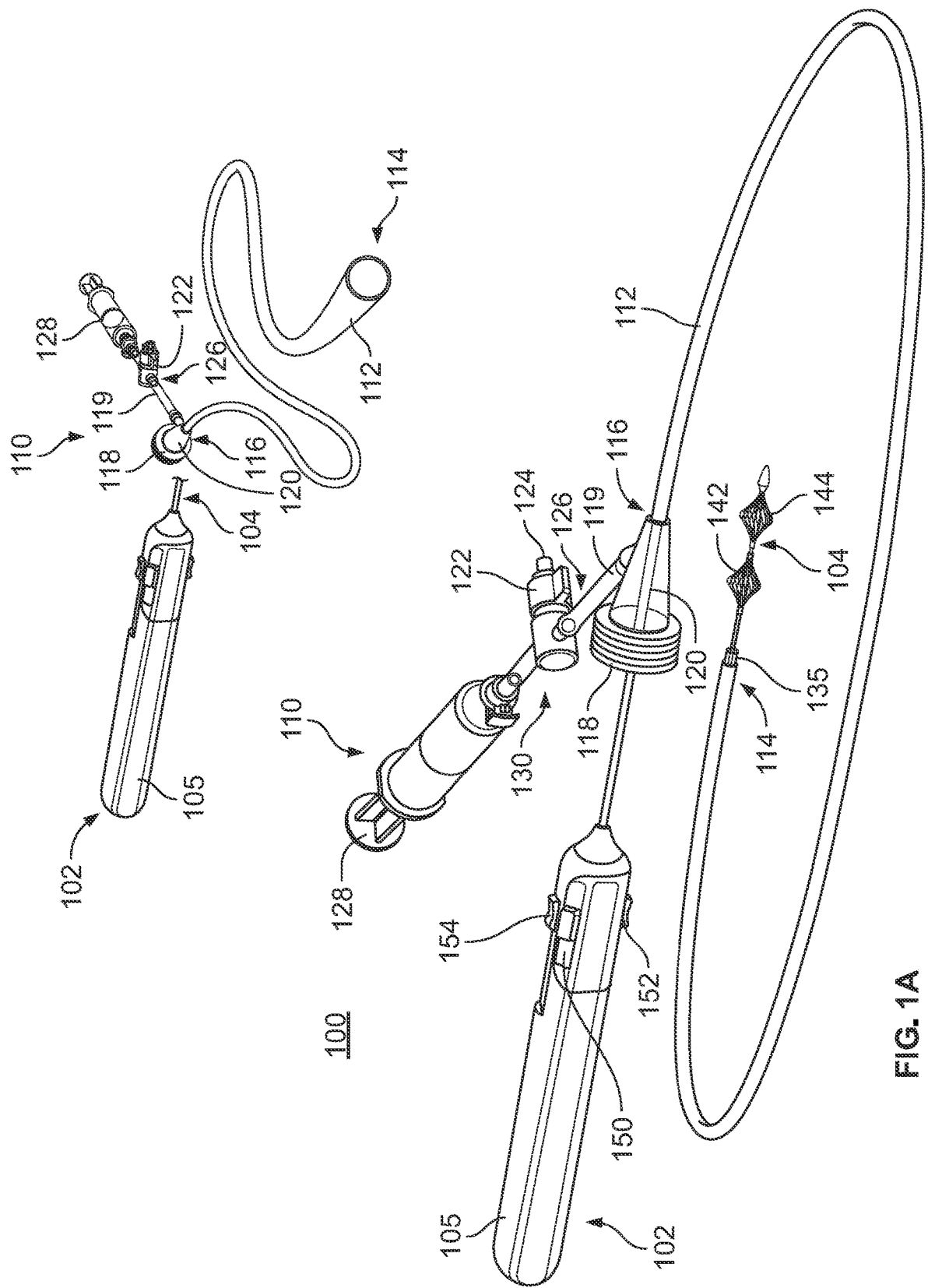
FIG. 1A illustrates a retrieval device, in accordance with some embodiments of the present specification.

FIG. 1A illustrates a retrieval device 100, in accordance with some embodiments of the present specification. The device 100 comprises a first unit 102 that includes a handle 105 coupled to a tip portion 104 via a plurality of telescoping tubes, wherein the handle 105 is configured to steer the tip portion 104 in proximity to an occlusion to perform thrombectomy. In some embodiments, a proximal element 142 and a distal element 144 are positioned on the tip portion 104.

The device 100 further comprises a second unit 110 that includes an aspiration catheter 112 having a distal end 114 and a proximal end 116. The proximal end 116 is coupled to a port 118 which, in embodiments of the present specification, includes a flexible lumen tube (or a valve) 120. In embodiments, the device 100 includes an aspiration port 119 which is distal to flexible lumen tube or valve 120. A hub 122 is coupled to a proximal end 126 of the aspiration port 119. A negative pressure source 128, such as, for example, a syringe, is coupled to a proximal end 130 of the hub 122. Activating or deactivating a button 124 on the hub 122 enables suction (from the negative pressure source 128) to be applied to or isolated from the aspiration catheter 112 via the aspiration port 119. In embodiments, aspiration catheter 112 is fabricated as a multiple layer catheter. In an embodiment, an innermost layer is made from polytetrafluoroethylene (PTFE); a middle layer is made using a laser-cut hypotube; and an outer layer that encapsulates the outer surface of the middle layer is fabricated from a material such as, and not limited to, a thermoplastic polyurethane, which includes an ultra-soft polyether or polyester-based blend (such as, but not limited to, NeuSoft). The multi-layer formation of aspiration catheter 112 enables the hypotube to maintain a largely spherical radius, even at a bend radius of less than 10 millimeters (mm), where the bend radius may range from 5 mm to 40 mm.

FIG. 1B illustrates a schematic view of the middle layer of aspiration catheter 112, in accordance with some embodiments of the present specification. Middle layer 160 is made from a material such as, but not limited to, stainless steel. Middle layer 160 is cylindrical and tubular, with an outer diameter of approximately (0.306±0.0005) mm and an inner diameter of approximately (0.292±0.002) mm, and a thickness of approximately 0.007 mm. A length of the middle layer 160 may range within (34.2±0.1) mm, which is divided into laser cut three parts. A first part 162 may extend from after approximately 0.02 mm of uncut layer on first end 164 of middle layer 160, for a length of approximately (10±0.1) mm. First part 162 has a pitch of 0.006. A second part 166 continues from first part 162 for a length of approximately (6±0.1) mm and has a pitch that transitions from 0.006 to 0.02 from the side continuing from first part 162 towards a third part 168. Third part 168 continues from second part 166 for a length of approximately 18.1 mm and maintains a pitch of 0.02. A remaining length of approximately 0.04 mm on second end 170 of middle layer 160 remain uncut.

During a thrombectomy procedure, the tip portion 104 is placed into a delivery catheter 135 and thereafter the delivery catheter 135 is inserted into the aspiration catheter 112 through the port 118, so that at least the tip portion 104 projects distally from the distal end 114 of the aspiration catheter 112. In accordance with aspects of the present specification, the device 100 is configured to enable an operator to single-handedly operate/actuate the handle portion 105 (using first, second and third knobs 150, 152 and 154) in order to mechanically extract occlusions, minimize tPA (tissue Plasminogen Activator), reduce bleeding, and aspirate by actuating the hub 122 while providing distal embolic protection.

In accordance with some aspects of the present specification, the first and second units 102, 110 are manufactured as separate standalone units or devices. This is advantageous in that a physician may use the first unit 102 with any third-party aspiration catheter.

In accordance with some embodiments, the tip 104 includes a pressure transducer/sensor to determine whether the negative pressure source 128 should be activated and for what duration of time. In some embodiments, a plurality of pressure signals generated by the pressure transducer are analyzed by a processor, implementing a plurality of instructions or programmatic code, to determine if the material being aspirated through the tip 104 is a mass of clot or just blood (in terms of the pressure the aspirated material generates at the tip 104 during aspiration). For example, a first average pressure value may be associated with the aspirated material being a mass of clot and a second average pressure value may be associated with the aspirated material being blood. The second average pressure value is substantially less than the first average pressure value. A pressure difference, corresponding to a difference between the first and second average pressure values, is indicative of the nature of the aspirated material. For example, a sudden drop in the average pressure value may be indicative that the aspirated material is only blood.

Accordingly, in some embodiments, if the aspirated material is determined to be only blood the processor stops or deactivates the negative pressure source 128. When the aspirated material is determined to be a mass of clot the processor reactivates the negative pressure source 128. This enables the negative pressure source 128 to be automated for precision and controlled aspiration. It should be appreciated that in various embodiments, the processor (along with the plurality of instructions or programmatic code) may reside locally within the retriever device 100 such as, for example, in the handle 105 or may be located remote from the device 100.

In various embodiments, the aspiration catheter 112 has a slim profile, can effectively anchor or self-center in a location, within a patient's vessel lumen, to better provide directed suction or vacuum/negative pressure, and/or can effectively funnel or direct suction or vacuum/negative pressure toward an occlusion or obstruction within the patient's vessel lumen. In accordance with some aspects of the present specification, the slim profile of the aspiration catheter 112 is indicative of a minimum bend radius without kinking. In various embodiments, the minimum bend radius is one of 16 French (5 mm), 20 French (15 mm) or 24 French (30 mm).

In various embodiments, the tip 104 is enabled to be self-centered within the patient's vessel lumen (without over-occluding the vessel) so that the tip 104 is pointed right at or slightly within the occlusion (or thrombus), so that when aspiration is applied, the suction or negative pressure is translated right to the occlusion and not to the vessel wall or other freely flowing blood. Stated differently, the catheter 112 enables directionality of the suction or negative pressure towards an occlusion.

The proximal element 142 and distal element 144 are positioned on the tip portion 104 to support centering of the tip of the aspiration catheter 112. In some embodiments, elements 142 and 144 are made from a mesh or a braided element. In a first state, elements 142 and 144 are constricted, and in a second state elements 142 and 144 are expanded into a spherical form. Specifically, when each element 142/144 is expanded to a specific radius, the peak of the expanded element is atraumatic, forms to the vessel lumen, and is able to move laterally such that each element 142/144 is able to bend back and forth, almost in a sweeping motion, as a physician moves aspiration catheter 112. The bend radius of each element stays above 0.05 inches to avoid permanent deformation. As movement of the aspiration catheter 112 stops, element 142/144 returns to shape without being permanently bent.

In accordance with some aspects of the present specification, directionality of the aspiration catheter 112 allows for a large external diameter of the catheter 112 for a much smoother, quicker transit of clot material into and through the catheter 112 without excessive blood loss. As mentioned before, handle 105 is configured to steer the tip portion 104 which is placed into delivery catheter 135 that is further inserted into aspiration catheter 112 through port 118. In embodiments, the tip portion 104 may be steered by maneuvering and steering aspiration catheter 112. Aspiration catheter 112 is made steerable by an axial pull wire that attaches from handle 105 to a distal tip of catheter 112. The pull wire is attached to a point on the circumference of the distal end of aspiration catheter 112 such that when force is exerted on the wire, catheter 112 deflects towards the side where the wire is attached. At the proximal end, the wire is attached to an actuator within handle 105. The actuator enables an operator to axially tension the wire.

Figure 1D:
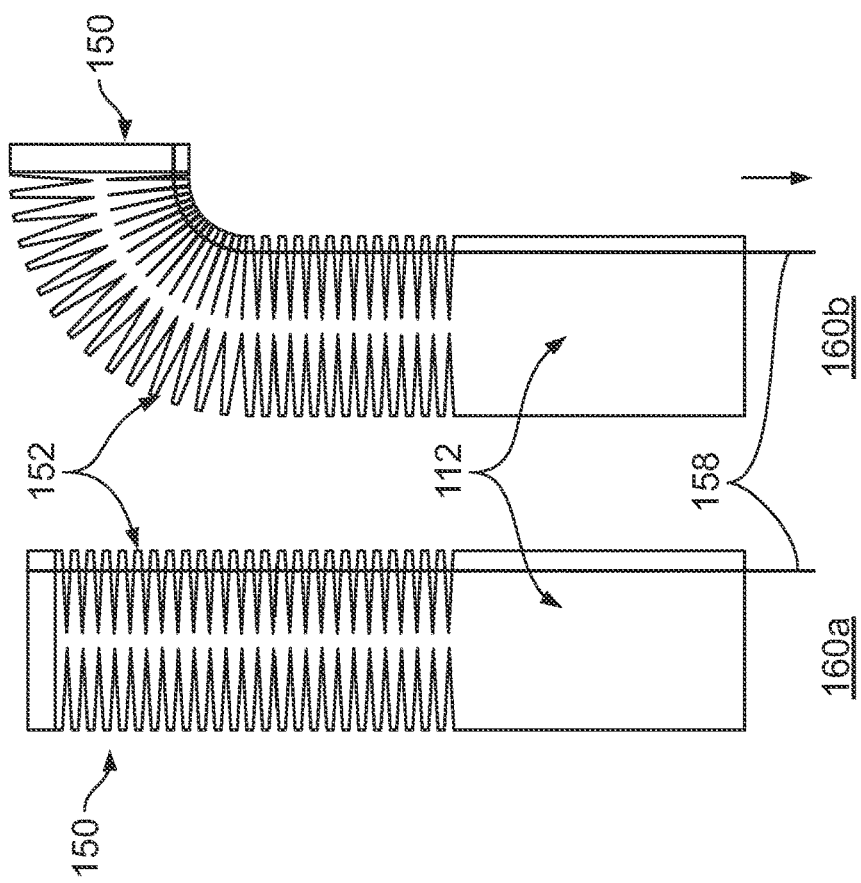
FIG. 1D is a schematic of an exemplary pull wire that is attached to an inner circumference of the distal tip at the distal end of a steerable catheter, in accordance with some embodiments of the present specification.
Figure 1C:
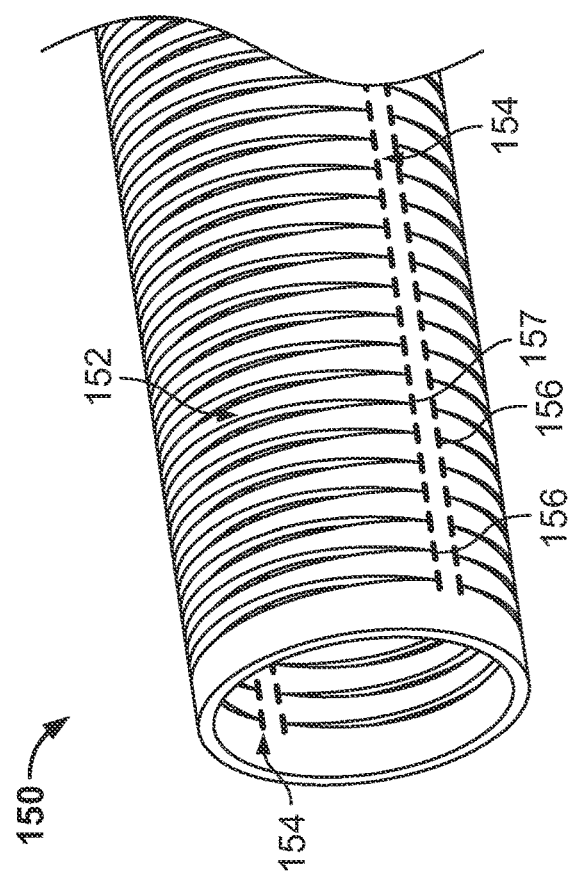
FIG. 1C shows an exemplary representation of a distal end of a steerable catheter in accordance with some embodiments of the present specification.

FIG. 1C illustrates an exemplary representation of a distal end 150 of a steerable catheter in accordance with some embodiments of the present specification. A laser-cut pattern 152 can be used in the hypotube at a distal end 150 of the catheter that is configured to facilitate actuation. Pattern 152 may resemble a 'Dogbone Pattern' where there are wedges of hypotube removed on either side of the tube with two axial spines 154 remaining which run down the neutral axis of distal end 150. Ends 156 of each wedge are strain relieved with a slot or hole 157 making the shape of pattern 152, in its entirety, resembling a dogbone shape.

FIG. 1D illustrates an exemplary schematic of a pull wire 158 that is attached to an inner circumference of the distal tip at a distal end 150 of a steerable catheter, in accordance with some embodiments of the present specification. Pull wire 158 is attached to a point on the circumference of distal end 150 such that when force is exerted on wire 158, catheter 112 deflects toward the side where wire 158 is attached. At the proximal end, the wire is attached to an actuator on handle 105 that enables an operator to axially tension wire 158. In the figure, a first view 160a illustrates distal end 150 in a straight configuration, or when wire 158 is not pulled. A second view 160b illustrates a bent distal end 150 when wire 158 is actuated. The steering mechanism described in FIGS. 1C and 1D can be applied to all of the embodiments of aspiration catheter 112 described subsequently in the present specification.

In accordance with some embodiments, the tip 104 includes a forward viewing element or camera sensor to enable a physician to visualize an occlusion within a patient's vessel lumen and accordingly optimize positioning of the tip 104.

The following sections disclose a plurality of embodiments of the aspiration catheter 112 describing various features and characteristics, in accordance with aspects of the present specification.

First Embodiment

Figure 2A:
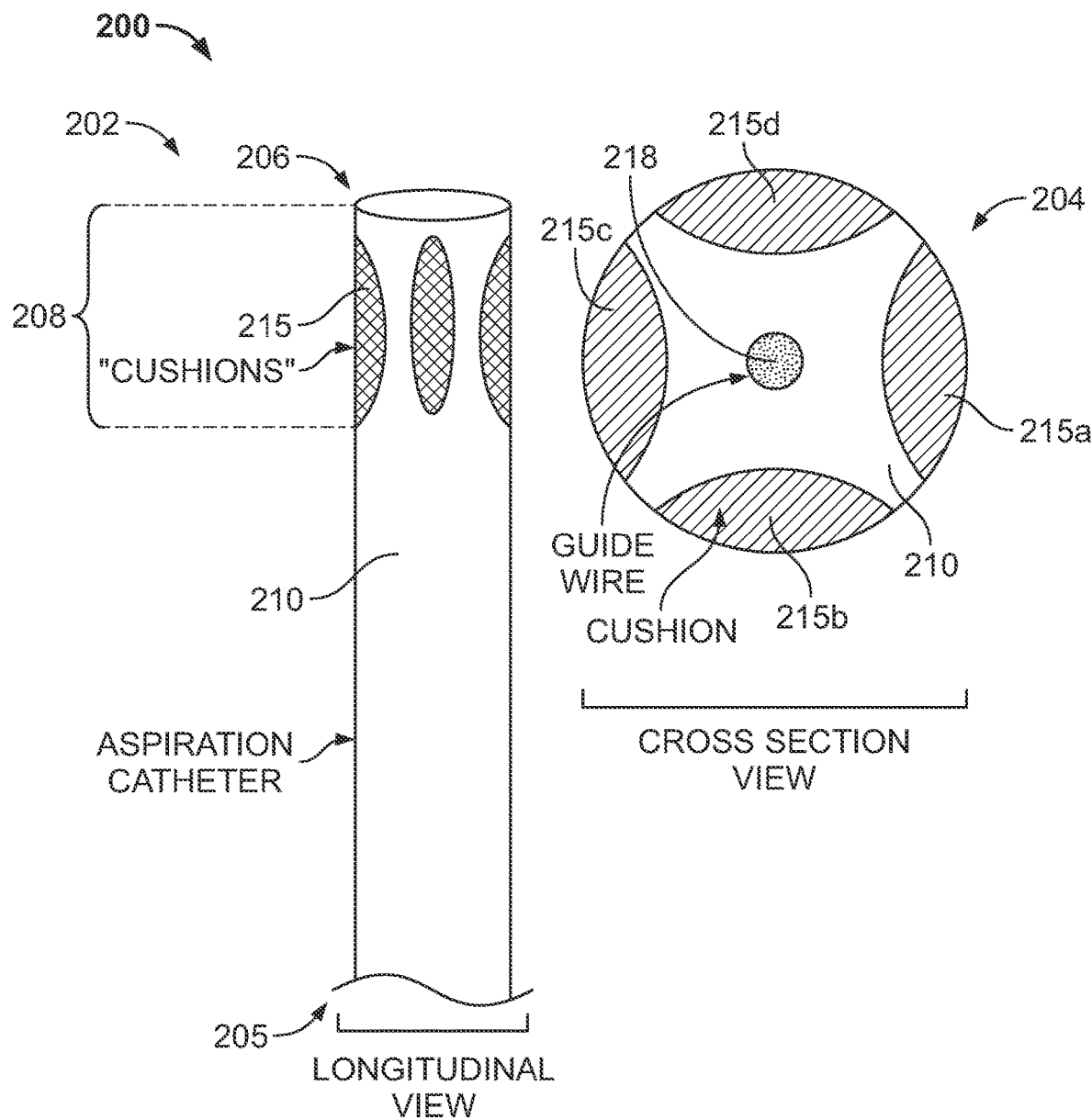
FIG. 2A illustrates a longitudinal view and a transverse cross-sectional view of an aspiration catheter, in accordance with some embodiments of the present specification.

FIG. 2A illustrates a longitudinal view 202 and a transverse cross-sectional view 204 of an aspiration catheter 200, in accordance with some embodiments of the present specification. The aspiration catheter 200 has a proximal end 205, a distal end 206 and a central lumen 210 leading to an opening at the distal end 206. A plurality of cavities or openings are formed at a tip 208 proximate the distal end 206. Each of the plurality of cavities or openings includes a centering member 215. In some embodiments, each centering member 215 is a tightly woven mesh or web having a substantially quadrangular cushion-like or hemispherical shape and which is in a first configuration while the catheter 200 is advanced into a patient's vessel lumen over a guide wire 218. In some embodiments, the first configuration corresponds to each centering member 215 being inverted, bulged or protruding into the lumen 210. In some embodiments, each centering member 215 is of Nitinol. In various embodiments, each centering member 215 is a mesh or web having triangular, quadrangular, hemispherical or polygonal shapes.

As shown in FIG. 2B, once the tip 208 is positioned at a desired location within the patient's vessel lumen 230 (see FIGS. 2C and 2D), in some embodiments, a wire 220 having a ball-shaped element 222 at a distal end 224 is advanced into the lumen 210 of the catheter 200. In some embodiments, an outer diameter of the ball-shaped element 222 is slightly less than an inner diameter of the lumen 210. As shown in FIG. 2C, the wire 220 is advanced through the lumen 210 until the ball-shaped element 222 hits the plurality of centering members 215. As the ball-shaped element 222 hits the plurality of centering members 215, each of the centering member 215 is forced or pushed (by the ball-shaped element 222) into a second configuration (from the earlier first configuration). In some embodiments, the second configuration corresponds to each centering member 215 being everted, bulged or protruding into the patient's vessel lumen 230 (outwardly from the lumen 210). Once the plurality of centering members 215 are in the second configuration, as shown in FIG. 2D, the wire 220 is retracted and removed from the lumen 210.

The plurality of centering members 215, in the second configuration, contact the inner walls of the patient's vessel lumen 230 and enable the tip 208 of the catheter 200 to be centered in the vessel lumen 230. Thus, the aspiration catheter 200 is characterized by the tip 208 that is capable of being dilated and self-centering within the vessel lumen 230.

In some embodiments, the tip 208 includes at least four centering members 215. In some embodiments, each pair (of the four members 215) is positioned diametrically opposite to each other around the circular cross-section of the lumen 210. Thus, in embodiments where the tip 208 includes first, second, third and fourth centering members 215a, 215b, 215c, 215d—the first and second centering members 215a, 215b are positioned diametrically opposite to each other, the third and fourth centering members 215c, 215d are also positioned diametrically opposite to each other and the first, second, third and fourth centering members 215a, 215b, 215c, 215d are separated by an angle of 90 degrees from each other around the circular cross-section of the lumen 210. Stated differently, the first and second centering members 215a, 215b are positioned at two opposite ends of a first diameter of the circular cross-section of the lumen 210, the third and fourth centering members 215c, 215d are positioned at two opposite ends of a second diameter of the circular cross-section of the lumen 210 and the first and second diameters intersect each other at 90 degrees. In alternate embodiments, the tip 208 includes more than four members 215.

In some embodiments, the plurality of centering members 215 are positioned at a distance 'd' from the distal end 206. In some embodiments, the distance 'd' ranges from 1 mm to 15 mm.

Figure 2E:
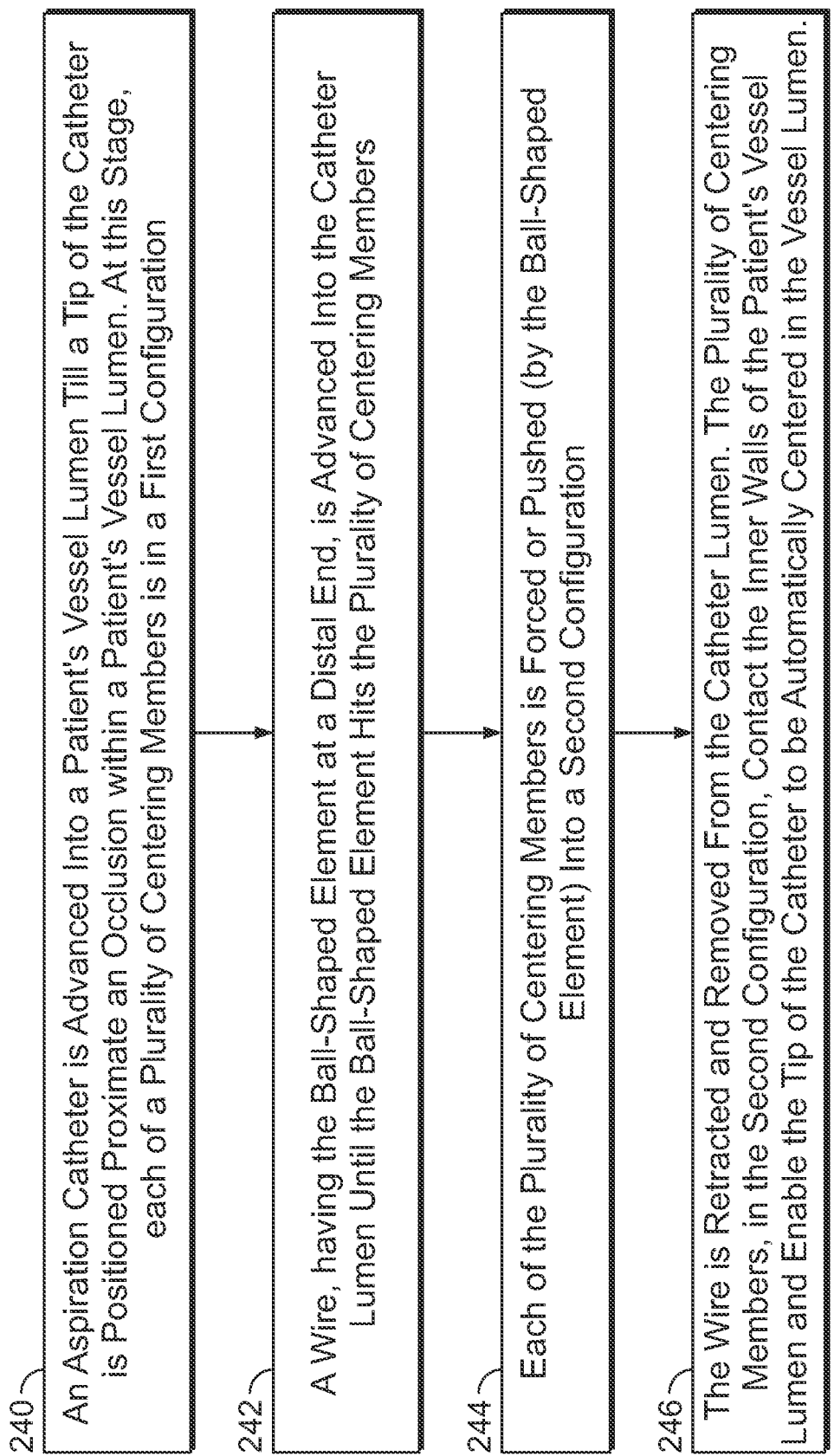
FIG. 2E is a flowchart of a plurality of exemplary steps of a method of centering the aspiration catheter of FIG. 2A within a patient's vessel lumen, in accordance with some embodiments of the present specification.

FIG. 2E is a flowchart of a plurality of exemplary steps of a method of centering the aspiration catheter 200 within a patient's vessel lumen, in accordance with some embodiments of the present specification. At step 240, the aspiration catheter 200 is advanced into the patient's vessel lumen till the tip 208 is positioned proximate an occlusion within the vessel lumen. At this stage, each of the plurality of centering members 215 is in the first configuration. In some embodiments, the first configuration corresponds to each centering member 215 being inverted, bulged or protruding into the lumen 210.

At step 242, the wire 220 having a shaped element, such as in an embodiment ball-shaped element 222, at the distal end 224, is advanced into the lumen 210 of the catheter 200 until the shaped element hits the plurality of centering members 215. At step 244, each of the plurality of centering members 215 is forced or pushed (by the shaped element) into the second configuration. In some embodiments, the second configuration corresponds to each centering member 215 being everted, bulged or protruding into the patient's vessel lumen.

At step 246, the wire 220 along with the shaped element is retracted and removed from the lumen 210. The plurality of centering members 215, in the second configuration, contact the inner walls of the patient's vessel lumen and enable the tip 208 of the catheter 200 to be automatically centered in the vessel lumen.

Second Embodiment

FIG. 3A illustrates a longitudinal view 302a and a transverse cross-sectional view 303a of an aspiration catheter 300 in a first configuration while FIG. 3B illustrates a longitudinal view 302b and a transverse cross-sectional view 303b of the aspiration catheter 300 within a patient's vessel lumen 330, in accordance with some embodiments of the present specification. The aspiration catheter 300 has a proximal end 305, a distal end 306 and a central lumen 310 leading to an opening 314 at the distal end 306. In some embodiments, the opening 314 is occluded and covered by a restraining cap.

A plurality of cavities or openings are formed at a tip 308 proximate the distal end 306. Each of the plurality of cavities or openings includes a centering member 315. In some embodiments, each centering member 315 is a tightly woven mesh or a web having a substantially quadrangular cushion-like or hemispherical shape and which is in a first configuration while the catheter 300 is advanced into the patient's vessel lumen 330 over a guide wire. In some embodiments, the first configuration corresponds to each centering member 315 being inverted, bulged or protruding into the lumen 310. In some embodiments, each centering member 315 is of a stretchable material. In various embodiments, each centering member 315 has triangular, quadrangular, hemispherical or polygonal shape.

As shown in FIG. 3B, once the tip 308 is positioned at a desired location within the patient's vessel lumen 330, in some embodiments, an indeflator is actuated to pump a fluid into the catheter lumen 310 through the proximal end 305 of the catheter 300. Since the opening 314 at the distal end 306 is occluded by the restraining cap, the pumped fluid increases hydrostatic pressure within the lumen 310 forcing the plurality of centering members 315 to transition from the first configuration to a second configuration. In some embodiments, the second configuration corresponds to each centering member 315 being everted, bulged or protruding into the patient's vessel lumen 330 (outwardly from the lumen 310).

In some embodiments, the restraining cap is configured to rupture once the hydrostatic pressure within the catheter lumen 310 reaches a predefined threshold value.

The plurality of centering members 315, in the second configuration, contact the inner walls of the patient's vessel lumen 330 and enable the tip 308 of the catheter 300 to be centered in the vessel lumen 330. Thus, the aspiration catheter 300 is characterized by the tip 308 that is capable of being dilated and self-centering within the vessel lumen 330.

In some embodiments, the tip 308 includes at least four centering members 315. In some embodiments, each pair (of the four members 315) is positioned diametrically opposite to each other around the circular cross-section of the lumen 310. Thus, in embodiments where the tip 308 includes first, second, third and fourth centering members 315a, 315b, 315c, 315d—the first and second centering members 315a, 315b are positioned diametrically opposite to each other, the third and fourth centering members 315c, 315d are also positioned diametrically opposite to each other and the first, second, third and fourth centering members 315a, 315b, 315c, 315d are separated by an angle of 90 degrees from each other around the circular cross-section of the lumen 310. Stated differently, the first and second centering members 315a, 315b are positioned at two opposite ends of a first diameter of the circular cross-section of the lumen 310, the third and fourth centering members 315c, 315d are positioned at two opposite ends of a second diameter of the circular cross-section of the lumen 310 and the first and second diameters intersect each other at 90 degrees. In alternate embodiments, the tip 308 includes more than four members 315.

In some embodiments, the plurality of centering members 315 are positioned at a distance 'd' from the distal end 306. In some embodiments, the distance 'd' ranges from 1 mm to 15 mm.

Figure 3C:
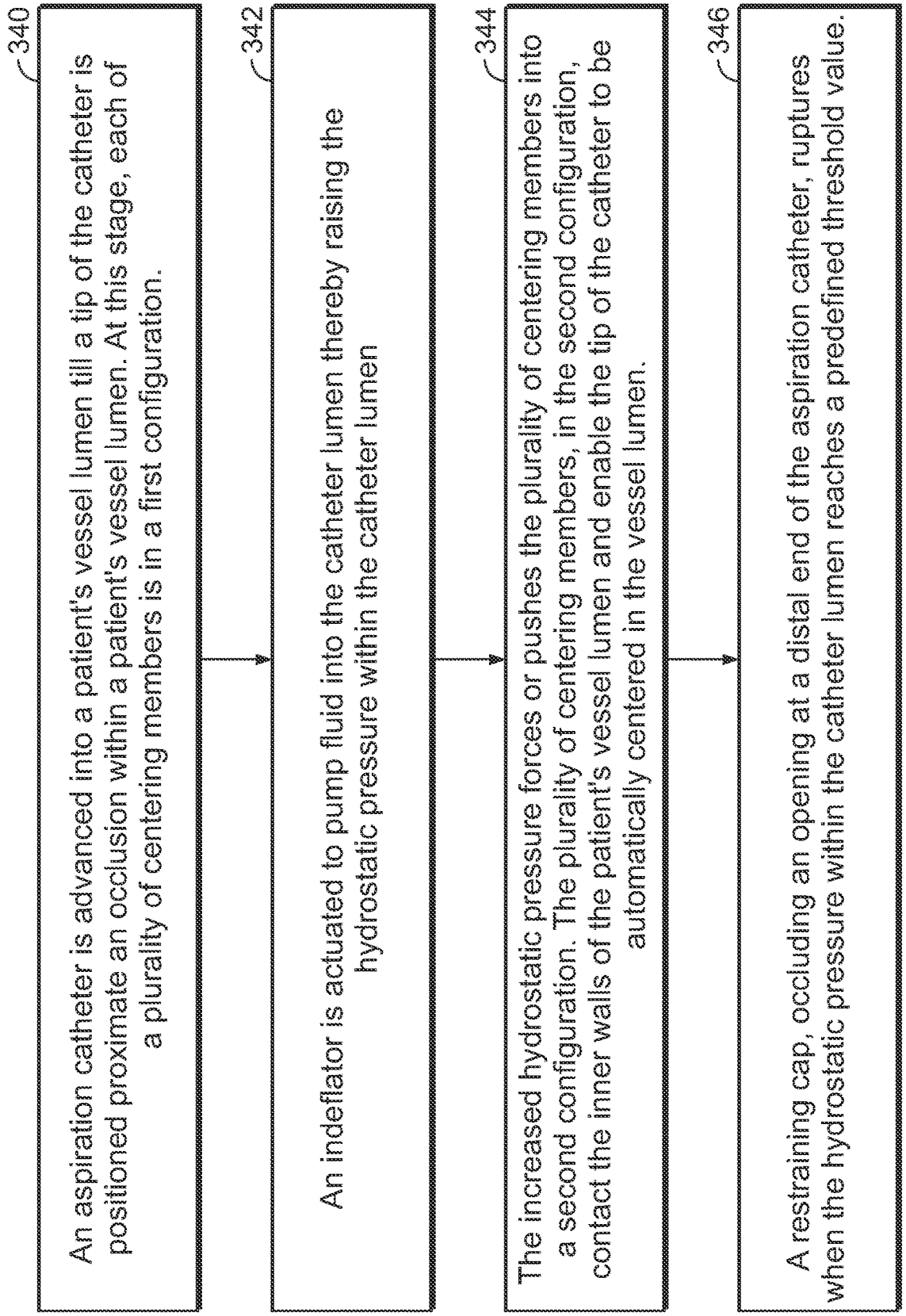
FIG. 3C is a flowchart of a plurality of exemplary steps of a method of centering the aspiration catheter of FIG. 3A within a patient's vessel lumen, in accordance with some embodiments of the present specification.

FIG. 3C is a flowchart of a plurality of exemplary steps of a method of centering the aspiration catheter 300 within a patient's vessel lumen, in accordance with some embodiments of the present specification. At step 340, the aspiration catheter 300 is advanced into the patient's vessel lumen till the tip 308 is positioned proximate an occlusion within the vessel lumen. At this stage, each of the plurality of centering members 315 is in the first configuration. In some embodiments, the first configuration corresponds to each centering member 315 being inverted, bulged or protruding into the lumen 310.

At step 342, an indeflator is actuated to pump fluid into the catheter lumen 310 thereby raising the hydrostatic pressure within the catheter lumen 310. At step 344, the increased hydrostatic pressure forces or pushes the plurality of centering members 315 into the second configuration. In some embodiments, the second configuration corresponds to each centering member 315 being everted, bulged or protruding into the patient's vessel lumen 330. The plurality of centering members 315, in the second configuration, contact the inner walls of the patient's vessel lumen and enable the tip 308 of the catheter 300 to be automatically centered in the vessel lumen 330.

At step 346, the restraining cap ruptures when the hydrostatic pressure within the catheter lumen 310 reaches a predefined threshold value. Thereafter, the indeflator may be deactivated.

Third Embodiment

FIG. 4A illustrates a longitudinal view of an aspiration catheter 400 positioned within a patient's vessel lumen 430 using a guide wire 403, in accordance with some embodiments of the present specification. The aspiration catheter 400 has a proximal end 405, a distal end 406 and a central lumen 410 leading to an opening at the distal end 406. In some embodiments, a catheter shaft 402 has a first outer diameter. In some embodiments, the first outer diameter is 24 French.

The catheter 400 has a tip 408 proximate the distal end 406. In some embodiments, the tip 408 has a proximal first portion 409p and a distal second portion 409d. In some embodiments, the first portion 409p has the first outer diameter in a first state and a second outer diameter in a second state, wherein the second outer diameter is greater than the first outer diameter. The first state corresponds to the first portion 409p being in a non-expanded or non-dilated configuration while the second state corresponds to the first portion 409p being in an expanded or dilated configuration. In embodiments, wall of the first portion 409p is redundant (using foldable material and/or thin collapsible foils) such that the first portion 409p can be transitioned from the first state to the second state, when desired, and vice-versa. In some embodiments, the second outer diameter ranges is greater than the first outer diameter by 0% to 438% (when the first outer diameter is 24 French, in an embodiment). The diameter may be adjusted to any level within this range.

In some embodiments, the second portion 409d tapers from the first outer diameter (proximate the first portion 409p) to a third outer diameter at the distal end 406, wherein the third outer diameter is less than the first outer diameter. In some embodiments, the third outer diameter is 22 French (when the first outer diameter is 24 French, in an embodiment). In various embodiments, the third outer diameter is 5% to 25% less than the first outer diameter.

In some embodiments, the tip 408 has an overall length ranging from 5 mm to 50 mm, and preferably 20 mm; the proximal first portion 409p has a length ranging from 4.5 mm to 54.5 mm, and preferably 18 mm; and the distal second portion 409d has a length ranging from 0.5 mm to 10 mm, and preferably 2 mm along a longitudinal axis of the catheter 400.

Once the tip 408 is positioned at a desired location within the patient's vessel lumen 430, the guide wire 403 is retracted and removed from the catheter lumen 410 as shown in FIG. 4B. Next, as shown in FIG. 4C, a wire 420 having a ball-shaped element 422 at a distal end 424 is advanced into the lumen 410 of the catheter 400. In embodiments, the outer diameter of the ball-shaped element 422 is slightly less than the first outer diameter but larger than the third outer diameter of the distal end 406. The wire 420 is advanced through the lumen 410 until the ball-shaped element 422 occludes the opening at the distal end 406 (since the outer diameter of the ball-shaped element 422 is greater than the third outer diameter of the distal end 406).

Once the distal end 406 is occluded, an indeflator 432 is actuated to pump a fluid into the catheter lumen 410 through the proximal end 405 of the catheter 400 as shown in FIG. 4D. Since the distal end 406 is occluded, the pumped fluid increases hydrostatic pressure within the lumen 410 forcing the first portion 409p to transition from the first state to the second state, as shown in FIG. 4E. The first portion 409p in the second state (expanded or dilated) partially occludes the vessel lumen 430 somewhat isolating a proximal region 440p of the vessel lumen 430 from a distal region 440d of the vessel lumen 430.

Additionally, in some embodiments, the first portion 409p, in the second state, contacts the inner walls of the patient's vessel lumen 430 enabling the tip 408 of the catheter 400 to be centered in the vessel lumen 430. Thus, the aspiration catheter 400 is characterized by a portion of the tip 408 that is capable of being dilated and enabling the tip 408 to be self-centering within the vessel lumen 430.

Thereafter the wire 420 is retracted and removed from the lumen 410 and, as shown in FIG. 4F, a retrieval device 440 (having a proximal element 440a and a distal element 440b) is advanced into the catheter lumen 410 to perform thrombectomy and capture an occlusion material (such as a thrombus or clot) from the vessel lumen 430.

Figure 4G:
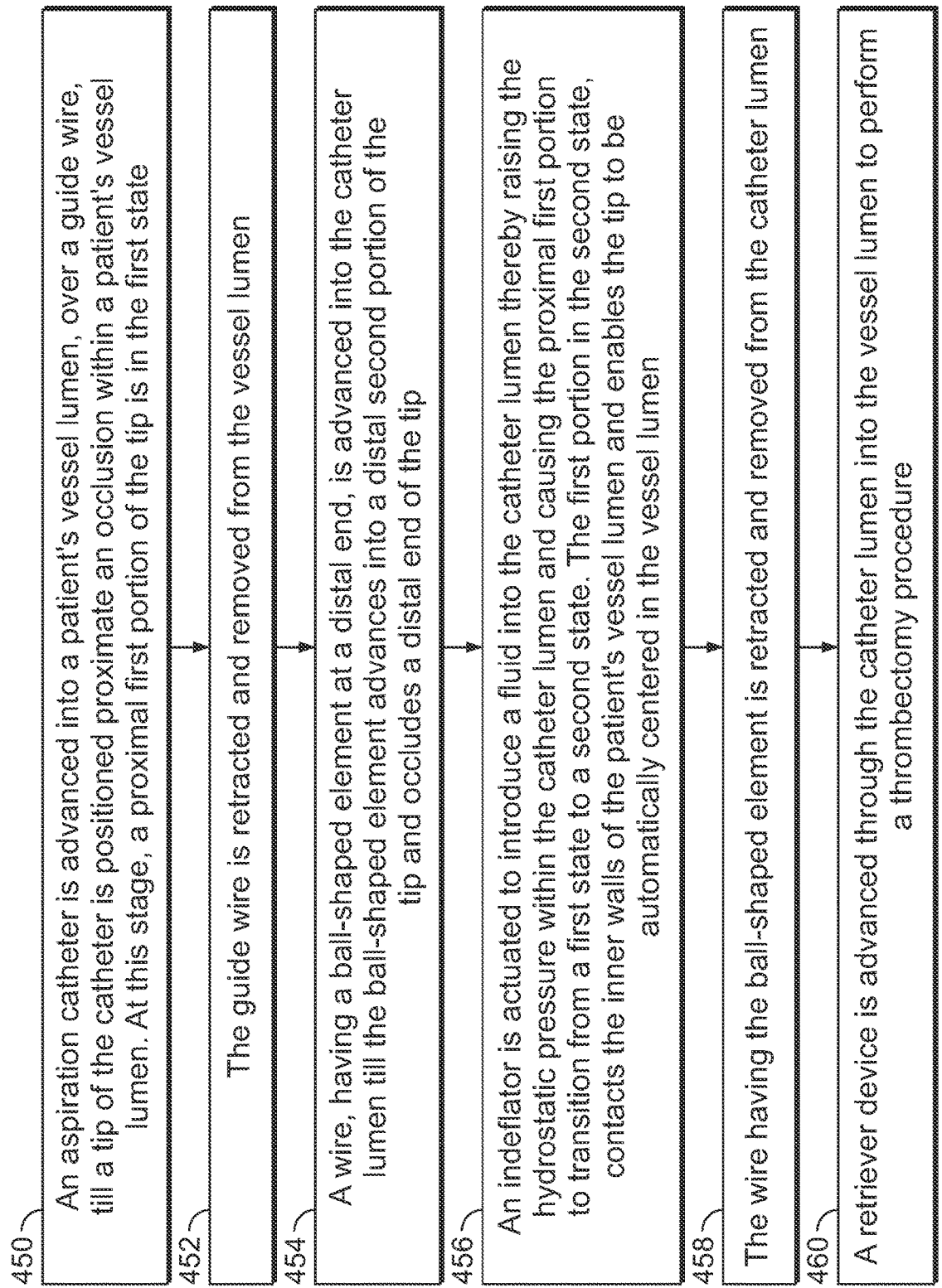
FIG. 4G is a flowchart of a plurality of exemplary steps of a method of centering the aspiration catheter of FIG. 4A within a patient's vessel lumen, in accordance with some embodiments of the present specification.

FIG. 4G is a flowchart of a plurality of exemplary steps of a method of centering the aspiration catheter 400 within the patient's vessel lumen 430, in accordance with some embodiments of the present specification. Referring now to FIGS. 4A through 4G, at step 450, the aspiration catheter 400 is advanced into the patient's vessel lumen 430, over the guide wire 403, till the tip 408 is positioned proximate an occlusion within the vessel lumen 430. At this stage, the proximal first portion 409p is in the first state—that is, non-expanded or non-dilated state so that the outer diameter of the first portion 409p is the same as the first outer diameter of the catheter shaft 402.

At step 452, the guide wire 403 is retracted and removed from the vessel lumen 430.

At step 454, the wire 420 having a shaped element, such as ball-shaped element 422, at the distal end 424, is advanced into the lumen 410 of the catheter 400 till the shaped element advances into the distal second portion 409d and occludes the distal end 406 of the tip 408 of the catheter 400 (since the distal second portion 409d tapers to the third outer diameter at the distal end 406, the third outer diameter being less than the first outer diameter of the catheter shaft 402.

At step 456, the indeflator 432 is actuated to introduce a fluid into the catheter lumen 410 thereby raising the hydrostatic pressure within the lumen 410 and causing the first portion 409p to transition from the first state to the second state, wherein the second state corresponds to the first portion 409p being in the expanded or dilated state. The first portion 409p in the second state, contacts the inner walls of the patient's vessel lumen 430 and enables the tip 408 of the catheter 400 to be automatically centered in the vessel lumen 430.

At step 458, the wire 420 is retracted and removed from the catheter lumen 410.

At step 460, the retriever device 440 is advanced into the catheter lumen 410 till a tip of the retriever device 440 extends beyond the distal end 406 of the catheter and proximate an occlusion within the vessel lumen 430. Thereafter, the proximal and distal elements 440a, 440b are expanded and used to remove the occlusion (that is, perform a thrombectomy procedure).

Fourth Embodiment

FIG. 5A illustrates a longitudinal view of an aspiration catheter 500 in a first state while FIG. 5B illustrates a longitudinal view of the aspiration catheter 500 in a second state and positioned within a patient's vessel lumen 530, in accordance with some embodiments of the present specification. The aspiration catheter 500 has a proximal end 505, a distal end 506 and a central lumen 510 leading to an opening at the distal end 506.

The catheter 500 has a tip 508 proximate the distal end 506. In some embodiments, the tip 508 includes a naturally self-expanding structure 515 such as, but not limited to, a balloon, stent or a self-expanding mesh of braided wires of Nitinol. In some embodiments, the structure 515 and therefore the tip 508 can be transitioned from a first state to a second state, when desired. The first state corresponds to the tip 508 being in a non-expanded or non-dilated configuration while the second state corresponds to the tip 508 being in an expanded or dilated configuration. In some embodiments, the structure 515 assumes a substantially spherical or elliptical shape in the second state. In some embodiments, the tip 508 has a length ranging from 0.5 mm to 20 mm along a longitudinal axis of the catheter 500.

In some embodiments, the structure 515 is restrained using a restraining member 522. In some embodiments, the restraining member 522 encompasses the structure 515 thereby restraining the structure 515 in the first state. In some embodiments, a distal end of a wire 520 is attached to the restraining member 522 so that the wire 520 extends from the restraining member 522 to the proximal end 505 of the catheter 500 within the lumen 510. In various embodiments, the restraining member 522 is configured as a ring or a cap such that it covers and restrains the expanding structure 515 to be in the first state. In various embodiments, the restraining member 522 is of a metal such as, but not limited to, stainless steel or of a plastic.

In some embodiments, once the tip 508 is positioned at a desired location within the patient's vessel lumen 530, the wire 520 is pulled at its proximal end causing the restraining member 522 to collapse into the catheter lumen 510 and be pulled out through the proximal end 505 of the catheter 500. Removal of the restraining member 522 causes the structure 515 (and, therefore, the tip 508) to automatically transition from the first state to the second state, as shown in FIG. 5B. The tip 508 in the second state (expanded or dilated) partially occludes the vessel lumen 530 isolating a proximal region 540p of the vessel lumen 530 from a distal region 540d of the vessel lumen 530.

The tip 508, in the second state, contacts the inner walls of the patient's vessel lumen 530 enabling the tip 508 of the catheter 500 to be centered in the vessel lumen 530. Thus, the aspiration catheter 500 is characterized by the tip 508 that is capable of being dilated thereby enabling the tip 508 to be self-centering within the vessel lumen 530.

In some embodiments, a catheter shaft 502 has a first outer diameter. In some embodiments, the tip 508 has the first outer diameter in the first state and a second outer diameter in the second state, wherein the second outer diameter is greater than the first outer diameter. In some embodiments, the second outer diameter is greater than the first outer diameter by 0% to 438%.

FIG. 5C is a flowchart of a plurality of exemplary steps of a method of centering the aspiration catheter 500 within the patient's vessel lumen 530, in accordance with some embodiments of the present specification. Referring now to FIGS. 5A through 5C, at step 550, the aspiration catheter 500 is advanced into the patient's vessel lumen 530 till the tip 508 is positioned proximate an occlusion within the vessel lumen 530. At this stage, the restraining member 522 restrains the expanding structure 515 to be in the first state—that is, non-expanded or non-dilated state. In some embodiments, at this stage, the outer diameter of the tip 508 is approximately the same as the first outer diameter of the catheter shaft 502.

At step 552, the wire 520 is pulled at its proximal end causing the restraining member 522 to uncover and release the structure 515 thereby transitioning the structure 515, and therefore the tip 508, from the first state to the second state, wherein the second state corresponds to the tip 508 being in the expanded or dilated state. The tip 508 in the second state, contacts the inner walls of the patient's vessel lumen 530 and enables the tip 508 of the catheter 500 to be automatically centered in the vessel lumen 530. In the second state, the tip 508 has the second outer diameter which is greater than the first outer diameter (of the tip 508 in the first state).

Pulling the wire 520 causes the restraining member 522 to collapse into the catheter lumen 510 and be pulled out through the proximal end 505 of the catheter 500.

Fifth Embodiment

Figures 6A, 6B:
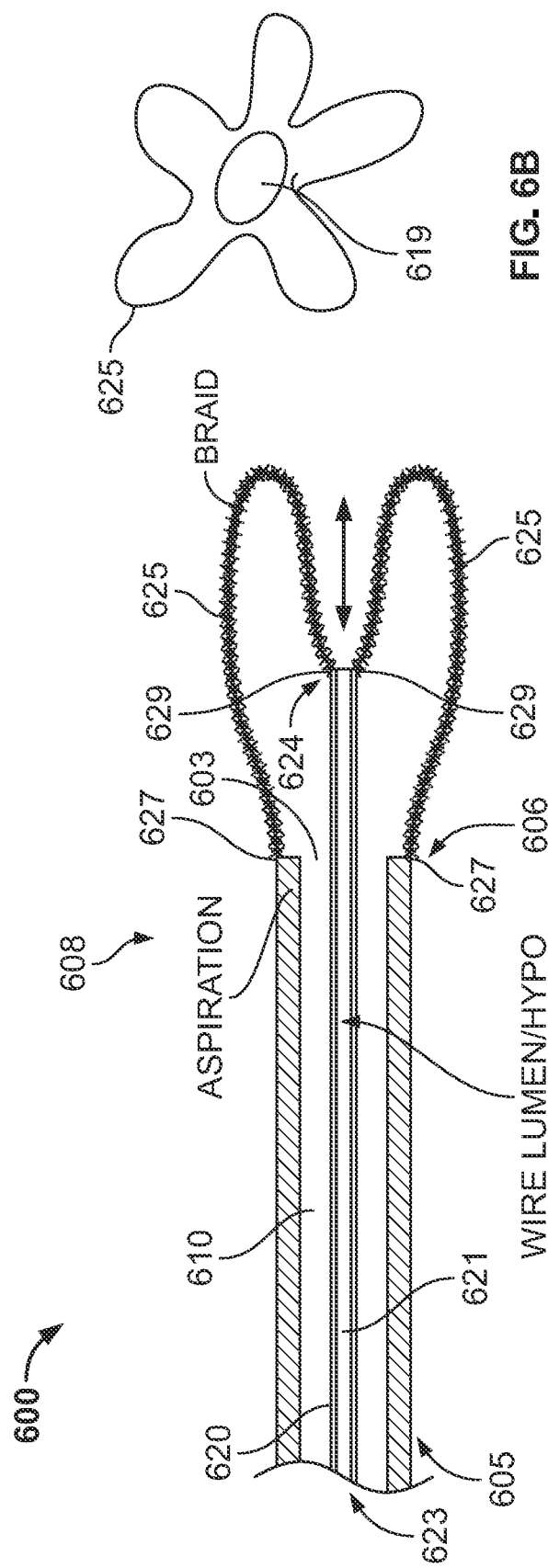
FIG. 6A illustrates a longitudinal cross-sectional view of an aspiration catheter, in accordance with some embodiments of the present specification.
FIG. 6B illustrates a side view of a tip of the aspiration catheter of FIG. 6A, in accordance with some embodiments of the present specification.

FIG. 6A illustrates a longitudinal cross-sectional view while FIG. 6B illustrates a side view of a tip 608 of an aspiration catheter 600, in accordance with some embodiments of the present specification. The aspiration catheter 600 has a proximal end 605, a distal end 606 and a central lumen 610 leading to an opening 603 at the distal end 606.

A wire 620 is positioned within the lumen 610. The wire 620 has a proximal end 623, a distal end 624 and a central lumen 621 with an opening 619 at the distal end 624. In some embodiments, the catheter 600 includes a plurality of braided wires 625 at the tip 608. Each braided wire 625 has a first end 627 and a second end 629. For each braided wire 625, the first end 627 is coupled or attached to the distal end 606 of the catheter 600 and the second end 629 is coupled or attached to the distal end 624 of the wire 620. Consequently, the first ends 627 of the plurality of braided wires 625 are attached around the perimeter of the opening 603 at the distal end 606 of the catheter 600 while the second ends 629 are attached around the perimeter of the opening 619 at the distal end 624 of the wire 620.

In some embodiments, each of the plurality of braided wire 625 has a length ranging from 10 mm to 70 mm, and preferably a length of 70 mm. In some embodiments, the plurality of braided wires 625 includes 8 to 122 number of braided wires, and preferably includes 32 wires.

Once the tip 608 is positioned at a desired location, such as, proximate an occlusion, within a patient's vessel lumen, the wire 620 is reciprocated axially by a physician—that is, moved proximally and distally, along a longitudinal axis of the catheter 600, to move the second ends 629 of the plurality of braided wires 625 while concurrently applying suction through the distal end 606 of the catheter 600. Movement of the wire 620 causes the plurality of braided wires 625 to change their collective configuration or shape while enabling the physician to scrape and break up the occlusion within the patient's vessel lumen. Thus, the catheter 600 enables simultaneous scraping/breaking of the occlusion as well as aspiration of the scraped/broken occlusion.

Figure 6C:
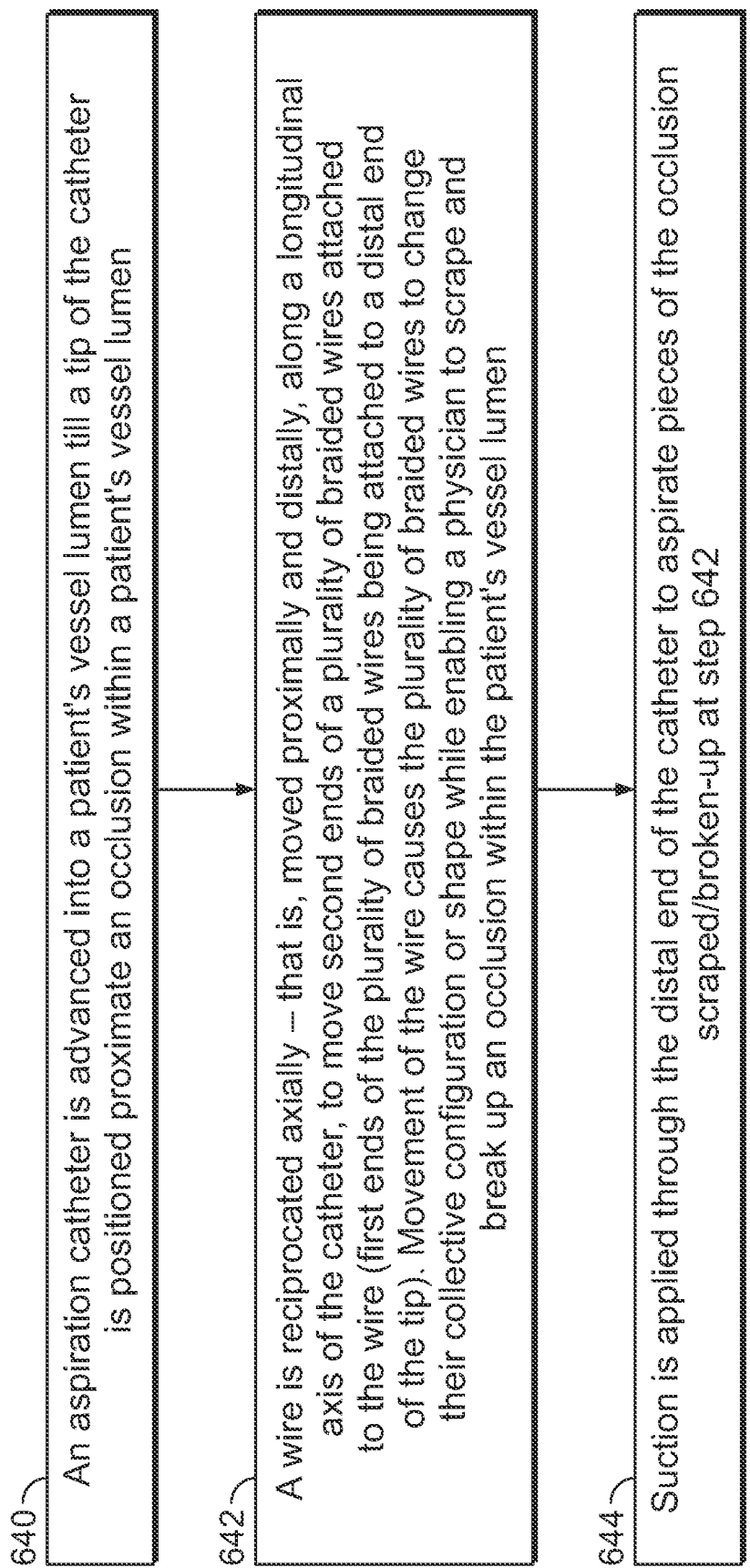
FIG. 6C is a flowchart of a plurality of exemplary steps of a method of using the aspiration catheter of FIG. 6A, within a patient's vessel lumen, in accordance with some embodiments of the present specification.

FIG. 6C is a flowchart of a plurality of exemplary steps of a method of using the aspiration catheter 600 within a patient's vessel lumen, in accordance with some embodiments of the present specification. At step 640, the aspiration catheter 600 is advanced into the patient's vessel lumen (over a guide wire, for example) till the tip 608 is positioned proximate an occlusion within the vessel lumen. At this stage, the wire 620 is positioned within the catheter lumen 610.

At step 642, the wire 620 is reciprocated axially—that is, moved proximally and distally, along a longitudinal axis of the catheter 600, to move the second ends 629 of the plurality of braided wires 625. Movement of the wire 620 causes the plurality of braided wires 625 to change their collective configuration or shape while enabling the physician to scrape and break up the occlusion within the patient's vessel lumen.

At step 644, suction is applied through the distal end 606 of the catheter 600 to aspirate pieces of the occlusion scraped/broken-up at step 642.

Sixth Embodiment

Figure 7A:
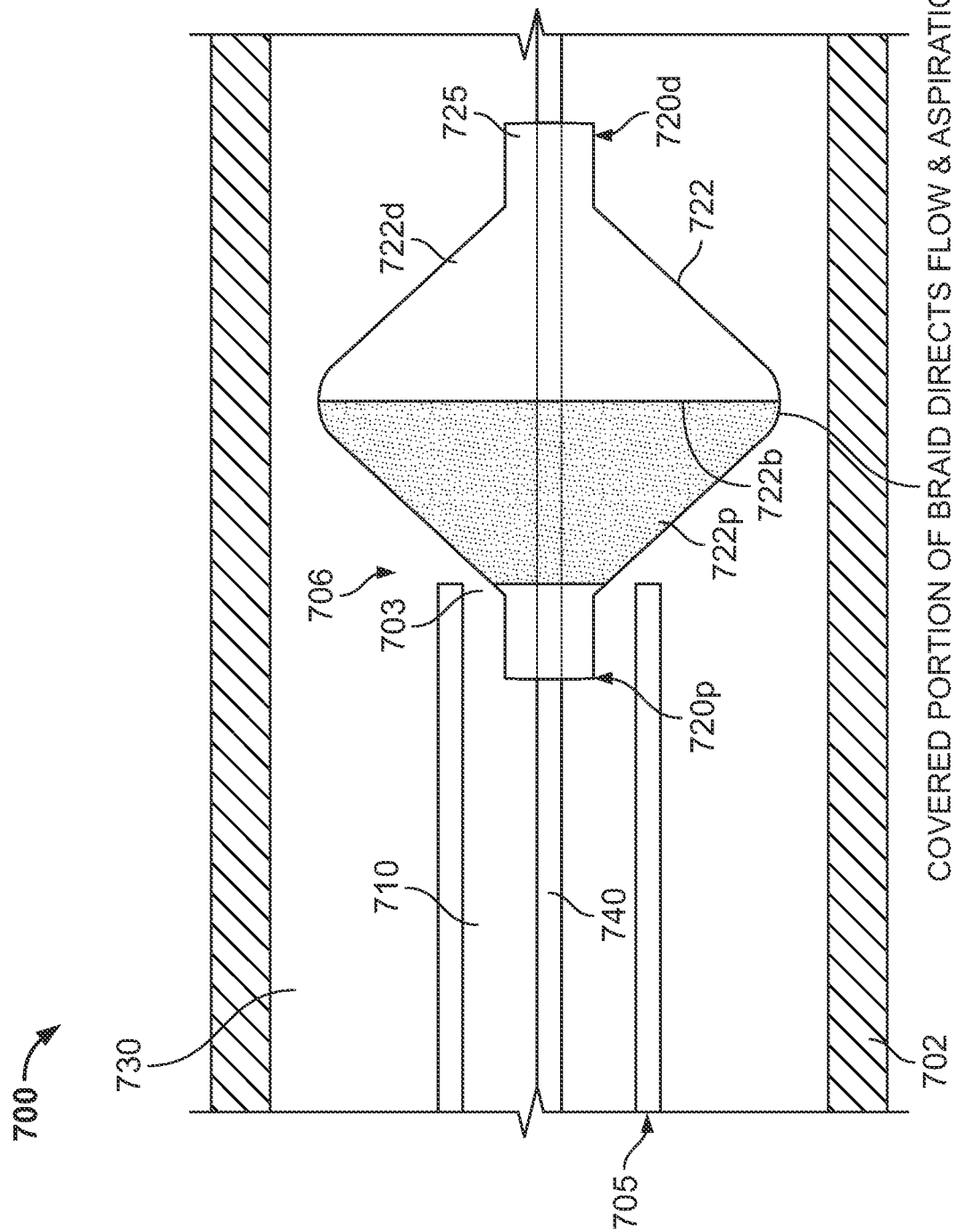
FIG. 7A illustrates a longitudinal cross-sectional view of an aspiration catheter positioned within a patient's vessel lumen, in accordance with some embodiments of the present specification.

FIG. 7A illustrates a longitudinal cross-sectional view of an aspiration catheter 700 positioned within a patient's vessel lumen 730, in accordance with some embodiments of the present specification. The aspiration catheter 700 has a proximal end 705, a distal end 706 and a central lumen 710 leading to an opening 703 at the distal end 706. The catheter 700 has a tip 708 proximate the distal end 706.

A structure 722 is attached to the opening 703 at the distal end 706. The structure 722 has proximal and distal ends 720p, 720d. A lumen or passage 725 extends from the proximal end 720p to the distal end 720d. In some embodiments, the lumen or passage 725 allows a retriever device 740 (which may or may not be passed within a delivery catheter), advanced into the catheter lumen 710, to pass through the structure 722 and into the lumen 730 of the patient's vessel 702. The retriever device 740 is used to scrape, dislodge, break-up and capture an occlusion (such as a clot or thrombus) within the vessel 702 during a thrombectomy procedure.

In some embodiments, the structure 722 has a three-dimensional geometric shape. In some embodiments, the structure 722 is characterized by a proximal first portion 722p and a distal second portion 722d. In some embodiments, each of the proximal first portion 722p and the distal second portion 722d has a funnel or substantially conical shape and their respective apexes point in opposite directions. In alternate embodiments, the structure 722 has a spherical, elliptical or pyramidal shape.

In some embodiments, the structure 722 is made of braided wires of stainless steel, for example. In some embodiments, the structure 722 is at least partially covered or coated. In some embodiments, the proximal first portion 722p is covered or coated to create a funneling effect and direct suction, through the aspiration catheter 700, substantially towards an occlusion within the vessel 702 (and not towards the walls of the vessel lumen). The funneling effect enables capturing of occlusion material (dislodged by the retriever device 740) and directing the occlusion material into the aspiration catheter 700 (and not around it).

Figure 7B:
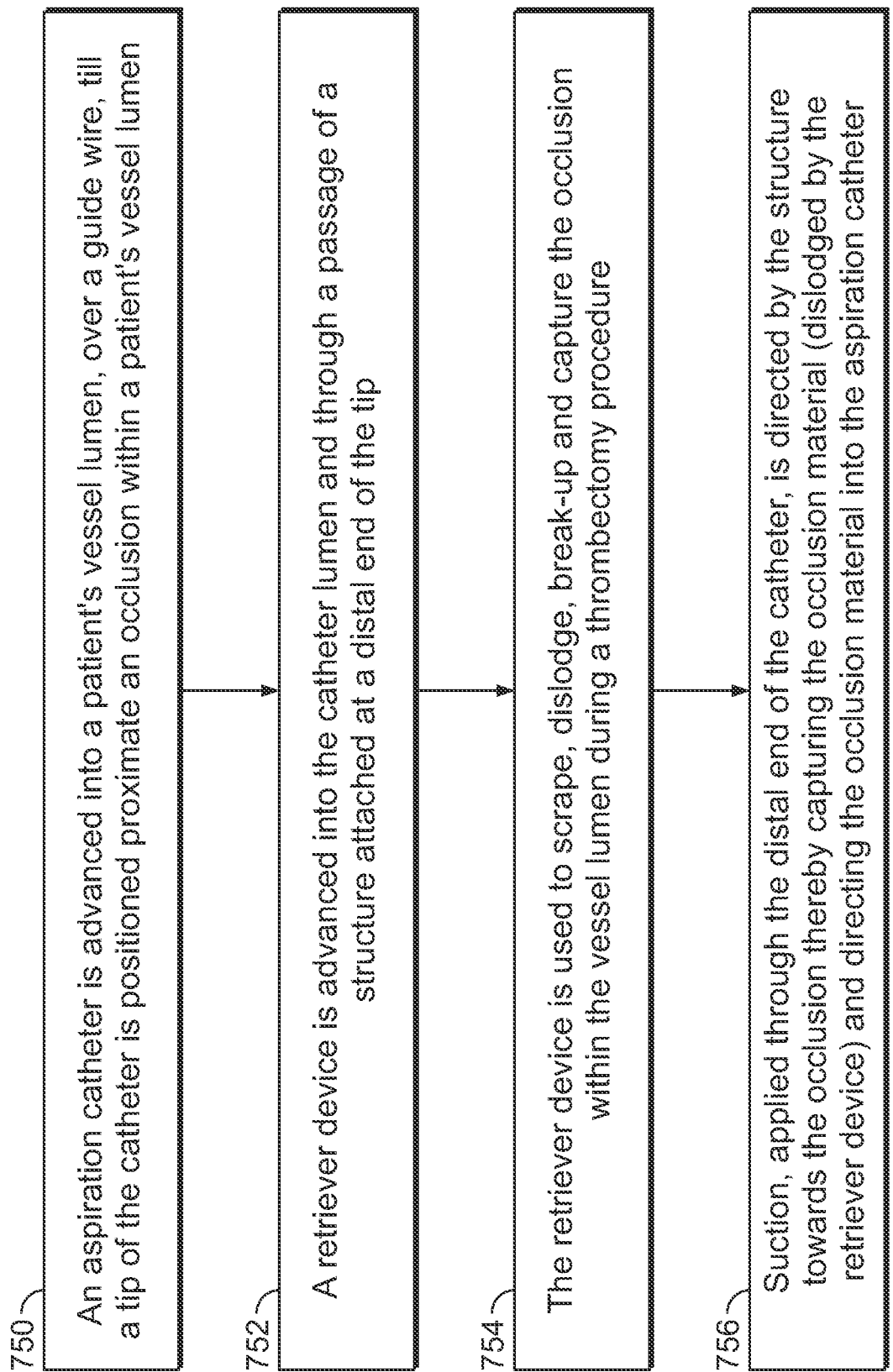
FIG. 7B is a flowchart of a plurality of exemplary steps of a method of using the aspiration catheter of FIG. 7A, within a patient's vessel lumen, in accordance with some embodiments of the present specification.

FIG. 7B is a flowchart of a plurality of exemplary steps of a method of using the aspiration catheter 700 within the patient's vessel lumen 730, in accordance with some embodiments of the present specification. At step 750, the aspiration catheter 700 is advanced into the patient's vessel lumen (over a guide wire, for example) till the tip 708 is positioned proximate an occlusion within the vessel lumen 730.

At step 752, the retriever device 740 is advanced into the catheter lumen 710 and through the passage 725 of the structure 722. At step 754, the retriever device 740 is used to scrape, dislodge, break-up and capture the occlusion (such as a clot) within the vessel 702 during a thrombectomy procedure.

At step 756, suction, applied through the distal end 706 of the catheter 700, is directed by the structure 722 towards the occlusion thereby capturing the occlusion material (dislodged by the retriever device 740) and directing the occlusion material into the aspiration catheter 700.

Seventh Embodiment

Figure 8A:
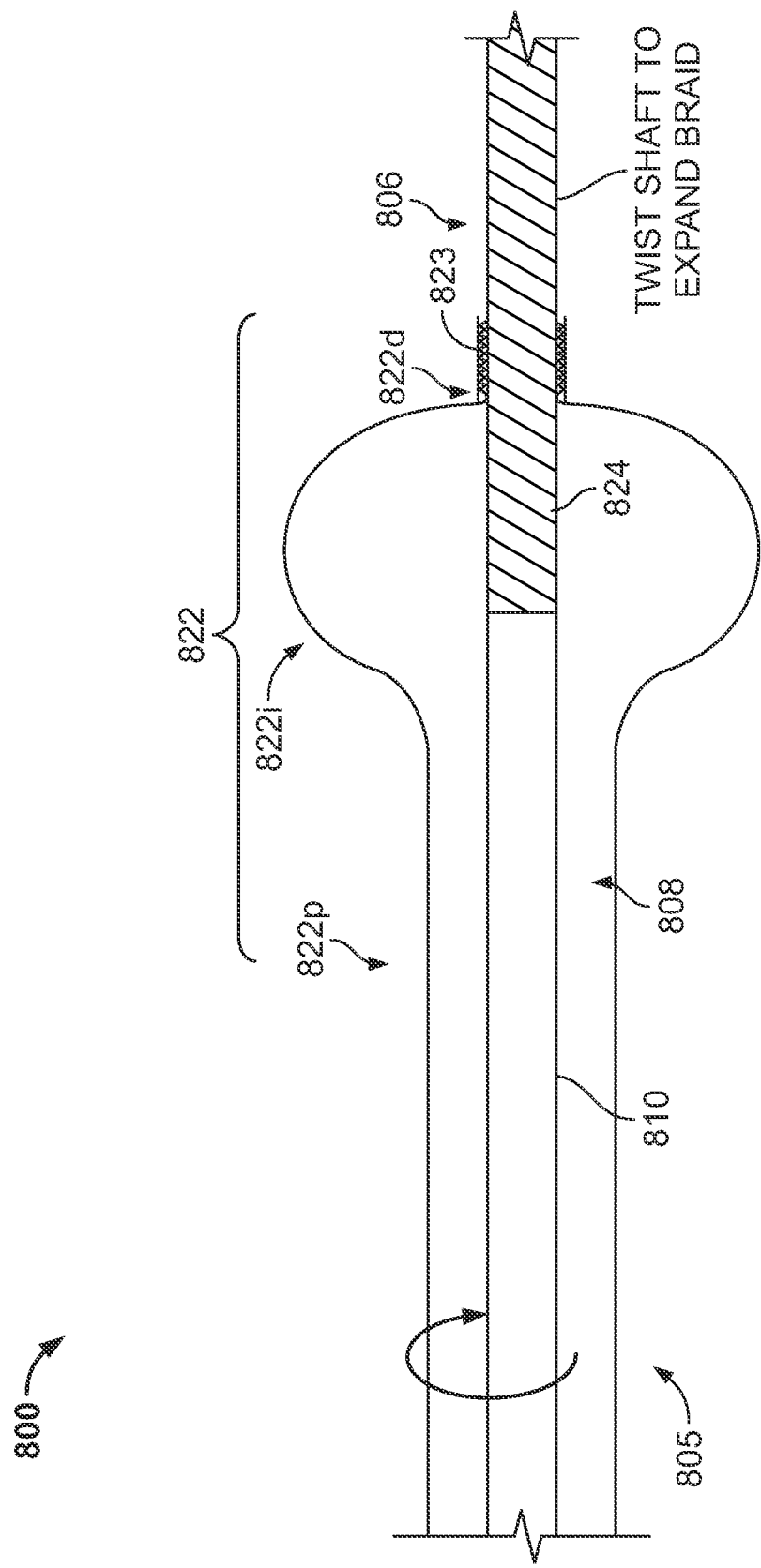
FIG. 8A illustrates a longitudinal cross-sectional view of an aspiration catheter, in accordance with some embodiments of the present specification.

FIG. 8A illustrates a longitudinal cross-sectional view of an aspiration catheter 800, in accordance with some embodiments of the present specification. The aspiration catheter 800 has a proximal end 805, a distal end 806 and a central lumen 810 leading to an opening at the distal end 806. The catheter 800 has a tip 808 proximate the distal end 806.

A structure 822 is positioned on the tip 808. In some embodiments, the structure 822 has a proximal portion 822p, an intermediate portion 822i and a distal portion 822d. The proximal portion 822p and the distal portion 822d are configured as hollow tubes, encompassing the tip 808. In embodiments, the proximal portion 822p is fabricated from one or a combination of any of the following: PTFE, urethane, nylon, stainless steel, nitinol, polyimide, and/or polyethylene terephthalate (PET). In embodiments, the distal portion 822d is fabricated from one or a combination of any of the following: stainless steel, nitinol, nylon, and/or PEEK. The proximal portion 822p is axially fixed relative to the catheter 800 while the distal portion 822d is free to move axially, relative to and along a longitudinal axis of the catheter 800, in proximal and distal directions.

In some embodiments, the intermediate portion 822i is a tightly woven mesh of a plurality of braided wires of, for example, stainless steel, nitinol, nylon, and/or PEEK. Therefore, the intermediate portion 822i may be made of different material than one or both of the proximal portion 822p and distal portion 822d (the ends), which may be made of a substantially more solid, less flexible material. In some embodiments, the intermediate portion 822i is configured to be transitioned from a first state to a second state, wherein the first state corresponds to the intermediate portion 822i being in a non-expanded configuration and the second state corresponds to the intermediate portion 822i being in an expanded configuration. In embodiments, the intermediate portion 822i assumes a three dimensional geometric shape in the second state. In various embodiments, the three dimensional geometric shape is substantially spherical or elliptical. In embodiments, the intermediate portion 822i assumes a substantially cylindrical shape, around the tip 808, in the first state.

An inner surface of the distal portion 822d has a first plurality of threads 823 that engage with associated second plurality of threads 824 formed on an outer surface of the catheter 800 (or tip 808) proximate the distal end 806. In embodiments, each of the first plurality of threads and the second plurality of threads has a length ranging from 3 mm to 40 mm. Thus, in embodiments, the outer surface of the catheter 800 (or tip 808) proximate the distal end includes a threaded portion having a length ranging from 3 mm to 40 mm. In embodiments, the length of the threads or threaded portion is dependent upon the diameter of the vessel in which the device of the present specification is deployed. For example, for use in the chambers of the heart, the threaded portion may be longer than for use a vessel having a smaller diameter. In embodiments, the number of threads may vary and can range from 1 thread all the way up to 120 threads. In embodiments, the use of one thread would push the catheter to one side of the vessel. In embodiments, the use of two or more threads would operate to center the catheter in the vessel. In embodiments, the threads may be formed of wires. In other embodiments, the threads may be cut as plastic strips forming a Malecot shape.

Once the tip 808 is positioned at a desired location, such as, proximate an occlusion within a patient's vessel lumen, the proximal end 805 of the catheter 800 is turned or rotated in a first direction causing the second plurality of threads 824 to engage with the first plurality of threads 823 and cause the distal portion 822d of the structure 822 to translate proximally (along a longitudinal axis of the catheter 800) thereby transitioning the intermediate portion 822i to the second state. Additionally, in some embodiments, the intermediate portion 822i, in the second state, contacts the inner walls of the patient's vessel lumen enabling the tip 808 of the catheter 800 to be centered in the vessel lumen. Thus, the aspiration catheter 800 is characterized by a portion of the tip 808 that is capable of being expanded and enabling the tip 808 to be self-centering within the vessel lumen. In embodiments, the intermediate portion 822i, in the second state, may expand by a length of 3 mm to 40 mm. Thus, the distal end can be moved the full length of the intermediate portion and may then meet the proximal portion.

Prior to removing the catheter 800 from the patient's vessel lumen, the proximal end 805 is turned or rotated in a second direction (opposite to the first direction) causing the second plurality of threads 824 to engage with the first plurality of threads 823 and cause the distal portion 822d of the structure 822 to translate distally (along a longitudinal axis of the catheter 800) thereby transitioning the intermediate portion 822i from the second state to the first state.

FIG. 8B is a flowchart of a plurality of exemplary steps of a method of centering the aspiration catheter 800 within a patient's vessel lumen, in accordance with some embodiments of the present specification. At step 850, the aspiration catheter 800 is advanced into the patient's vessel lumen (over a guide wire, for example) till the tip 808 is positioned proximate an occlusion within the patient's vessel lumen.

At step 852, the proximal end 805 of the catheter 800 is turned or rotated in a first direction causing the distal portion 822d of the structure 822 to translate proximally (along a longitudinal axis of the catheter 800) thereby transitioning the intermediate portion 822i to the second state (that is, into the expanded configuration). The intermediate portion 822i, in the second state, contacts the inner walls of the patient's vessel lumen enabling the tip 808 of the catheter 800 to be centered in the vessel lumen.

At step 854, a retriever device is advanced through the catheter lumen 810, during a thrombectomy procedure, to scrape, dislodge, break-up and capture the occlusion. At step 856, suction, applied through the distal end 806 of the catheter 800, is directed by the centered tip towards the occlusion thereby capturing the occlusion material (dislodged by the retriever device) and directing the occlusion material into the aspiration catheter 800.

At step 858, the proximal end 805 is turned or rotated in a second direction (opposite to the first direction) causing the distal portion 822d of the structure 822 to translate distally (along a longitudinal axis of the catheter 800) thereby transitioning the intermediate portion 822i from the second state to the first state (that is, into the non-expanded or non-dilated configuration). Thereafter, the catheter 800 and the retriever device are withdrawn from the vessel lumen at step 860.

Eighth Embodiment

Figure 9A:
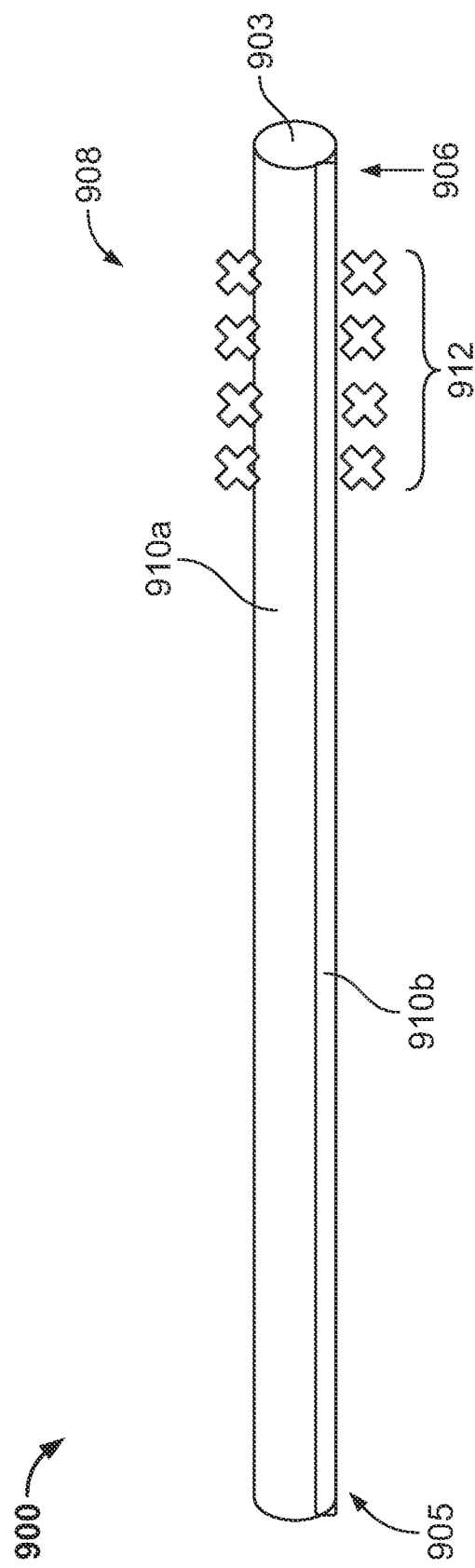
FIG. 9A illustrates a longitudinal cross-sectional view of an aspiration catheter, in accordance with some embodiments of the present specification.

FIG. 9A illustrates a longitudinal cross-sectional view of an aspiration catheter 900, in accordance with some embodiments of the present specification. The aspiration catheter 900 has a proximal end 905, a distal end 906, a first lumen 910a leading to a first opening at the distal end 906 and a second lumen 910b leading to a second opening at the distal end 906. The catheter 900 has a tip 908 proximate the distal end 906.

The first opening is occluded with a member 903. In some embodiments, the member 903 is configured as a cap or a plug. In some embodiments, the catheter 900 is configured to be transitioned from a first state to a second state. The first state corresponds to the catheter 900 being in a non-expanded configuration and having a first outer diameter. The second state corresponds to the catheter 900 being in an expanded or dilated configuration and having a second outer diameter. In embodiments, the second diameter is greater than the first diameter.

In embodiments, wall of the catheter 900 is redundant (using foldable material and/or thin collapsible foils) such that the catheter can be transitioned from the first state to the second state, when desired.

In some embodiments, the catheter 900 is advanced into a patient's vessel lumen over a guide wire that passes through the second lumen. Once the tip 908 is positioned at a desired location, such as, proximate an occlusion within the patient's vessel lumen, an indeflator (coupled to the proximal end of the catheter 900) is actuated to pump a fluid into the first lumen 910a thereby raising the hydrostatic pressure within the first lumen 910a since the first opening is occluded by the member 903. The raised hydrostatic pressure causes the catheter 900 to transition from the first state to the second state. The member 903 is configured to rupture when the hydrostatic pressure reaches a predefined threshold value.

In some embodiments, the tip 908 has a plurality of scrapers 912 to scrape, dislodge, capture and pull out the occlusion.

Figure 9B:
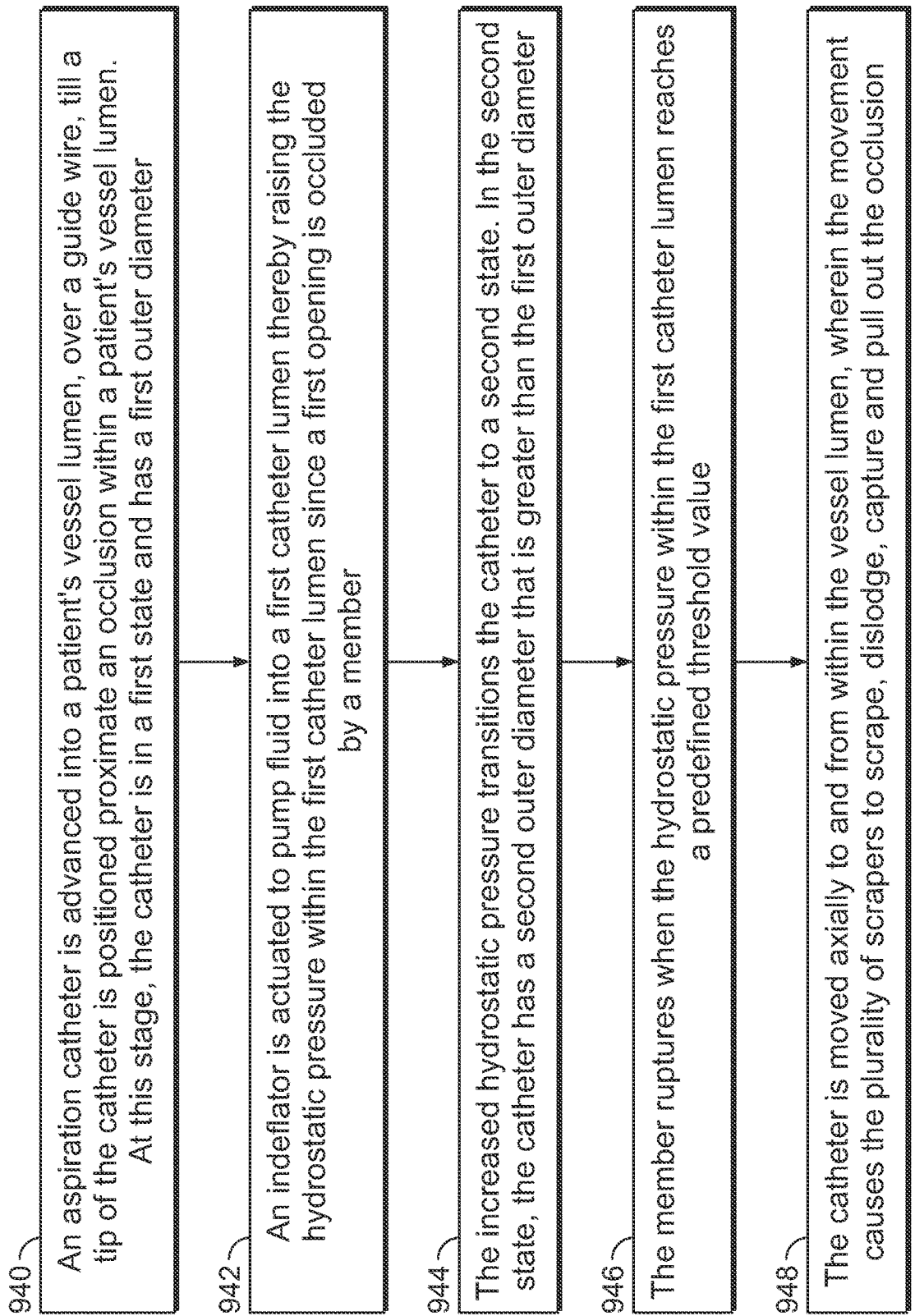
FIG. 9B is a flowchart of a plurality of exemplary steps of a method of using the aspiration catheter of FIG. 9A within a patient's vessel lumen, in accordance with some embodiments of the present specification.

FIG. 9B is a flowchart of a plurality of exemplary steps of a method of using the aspiration catheter 900 within a patient's vessel lumen, in accordance with some embodiments of the present specification. At step 940, the aspiration catheter 900 is advanced into the patient's vessel lumen (over a guide wire passing through the second lumen 910b) till the tip 908 is positioned proximate an occlusion within the vessel lumen. At this stage, the catheter is in the first state and has a first outer diameter. In some embodiments, the first outer diameter is 4 French.

At step 942, an indeflator is actuated to pump fluid into the first lumen 910a thereby raising the hydrostatic pressure within the first lumen 910a since the first opening is occluded by the member 903. At step 944, the increased hydrostatic pressure transitions the catheter 900 to the second state. In the second state, the catheter has a second outer diameter that is greater than the first outer diameter. In some embodiments, the second outer diameter is 20 French.

At step 946, the member 903 ruptures when the hydrostatic pressure within the first lumen 910a reaches a predefined threshold value. Thereafter, the indeflator may be deactivated.

At step 948, the catheter 900 is moved axially to and from within the vessel lumen, wherein the movement causes the plurality of scrapers 912 to scrape, dislodge, capture and pull out the occlusion.

The above examples are merely illustrative of the many applications of the devices of the present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An aspiration catheter having a proximal end, a distal end and a lumen extending between the proximal end and the distal end and configured to receive a second catheter, wherein the distal end comprises:
  a proximal portion, wherein the proximal portion comprises a first solid material defining a first hollow, enclosed tube;
  a distal portion, wherein the distal portion comprises a second solid material defining a second hollow, enclosed tube, wherein the distal portion is configured to move in a proximal direction and a distal direction along a longitudinal axis of the distal end, and wherein an inner surface of the distal portion comprises a first plurality of threads configured to engage with a second plurality of threads formed on an outer surface of a distal end of the second catheter; and
  an intermediate portion coupled to and extending between the proximal portion and the distal portion, wherein the intermediate portion comprises a flexible material that is different than the first solid material and the second solid material, wherein the intermediate portion has at least a first state and a second state, and wherein movement of the proximal end in a first direction causes the distal portion to translate proximally, thereby transitioning the intermediate portion to the second state, and wherein movement of the proximal end in a second direction, opposite to the first direction, causes the distal portion to translate distally thereby transitioning the intermediate portion to the first state.

2. The aspiration catheter of claim 1, wherein the first solid material is one or a combination of the following materials: PTFE, urethane, nylon, stainless steel, nitinol, polyimide, and/or polyethylene terephthalate (PET) and the second solid material is one or a combination of the following materials: stainless steel, nitinol, nylon, and/or PEEK.

3. The aspiration catheter of claim 1, wherein the first state corresponds to the intermediate portion being in a substantially linear, non-expanded configuration.

4. The aspiration catheter of claim 1, wherein the second state corresponds to the intermediate portion being in an expanded configuration and wherein, in the expanded configuration, the intermediate portion acquires a substantially spherical, cylindrical, or elliptical shape in the second state.

5. The aspiration catheter of claim 1, wherein the intermediate portion is a mesh of braided wires.

6. The aspiration catheter of claim 1, wherein the movement of the proximal end in the first direction or second direction is a rotation of the proximal end.

7. The aspiration catheter of claim 1, wherein a length of each of the first plurality of threads and the second plurality of threads is in a range of 3 mm to 40 mm.

8. The aspiration catheter of claim 1, wherein the inner surface of the distal portion comprises a first plurality of threads configured to engage with a second plurality of threads formed on the outer surface of the distal end of the second catheter.

9. The aspiration catheter of claim 8, wherein rotation of the proximal end in the first direction causes the distal portion to translate proximally via the engagement of the first plurality of threads and the second plurality of threads, thereby transitioning the intermediate portion to the second state.

10. The aspiration catheter of claim 8, wherein rotation of the proximal end in the second direction, opposite to the first direction, causes the distal portion to translate distally via the engagement of the first plurality of threads and the second plurality of threads, thereby transitioning the intermediate portion to the first state.

11. A method of centering a tip of an aspiration catheter within a patient's vessel lumen, said aspiration catheter having a proximal end, a distal end, and a lumen extending between the proximal end and the distal end and configured to receive a second catheter, said tip being proximate the distal end, wherein a structure is positioned at the tip, said structure having a proximal portion, an intermediate portion, and a distal portion, wherein the proximal portion is fixed, the intermediate portion is coupled to and extends between the proximal portion and distal portion and is in a first state and the distal portion is free to move in proximal and distal directions along a longitudinal axis of the distal end of the aspiration catheter, and wherein an inner surface of the distal portion has a first plurality of threads configured to engage with a second plurality of threads formed on an outer surface of a distal end of the second catheter, the method comprising:
   positioning the tip proximate an occlusion within the vessel lumen;
   moving the proximal end of the catheter in a first direction to translate the distal portion of the structure proximally thereby transitioning the intermediate portion to a second state, wherein the intermediate portion in the second state contacts inner walls of the vessel lumen enabling the tip to be centered in the vessel lumen;
   advancing a device into the catheter lumen and through the opening for dislodging the occlusion; and
   applying suction through the distal end of the catheter, wherein the centered tip directs said suction towards the occlusion thereby capturing and directing the occlusion into the catheter.

12. The method of claim 11, further comprising: moving the proximal end in a second direction opposite to the first direction to translate the distal portion distally thereby transitioning the intermediate portion to the first state; and withdrawing the catheter and the device from the vessel lumen.

13. The method of claim 11, wherein the proximal and distal portions are hollow tubes encompassing the tip.

14. The method of claim 11, wherein the first state corresponds to the intermediate portion being in a substantially linear, non-expanded configuration.

15. The method of claim 11, wherein the second state corresponds to the intermediate portion being in an expanded configuration and wherein, in the expanded configuration, the intermediate portion acquires a substantially spherical, cylindrical, or elliptical shape in the second state.

16. The method of claim 11, wherein the intermediate portion is a mesh of braided wires.

17. The method of claim 11, wherein the movement of the proximal end in the first direction or second direction is a rotation of the proximal end.

18. The aspiration catheter of claim 11, wherein a length of each of the first plurality of threads and of the second plurality of threads is in a range of 3 mm to 40 mm.

19. The aspiration catheter of claim 11, wherein movement of the proximal end in the first direction causes the distal portion to translate proximally via the engagement of the first plurality of threads and the second plurality of threads, thereby transitioning the intermediate portion to the second state.

20. The aspiration catheter of claim 11, wherein movement of the proximal end in the second direction, opposite to the first direction, causes the distal portion to translate distally via the engagement of the first plurality of threads and the second plurality of threads, thereby transitioning the intermediate portion to the first state.

* * * * *